United States Patent
Kutateladze et al.

(10) Patent No.: US 8,735,167 B2
(45) Date of Patent: *May 27, 2014

(54) PHOTOINDUCED SIGNAL AMPLIFICATION THROUGH EXTERNALLY SENSITIZED PHOTOFRAGMENTATION IN MASKED PHOTOSENSITIZERS AND PHOTOAMPLIFIED FLUORESCENCE TURN-OFF SYSTEM

(75) Inventors: Andrei G. Kutateladze, Centennial, CO (US); Alexei Kurchan, Piscataway, NJ (US); Rudresha Kottani, Tucson, AZ (US); Janaki Majjigapu, Menomonee, WI (US)

(73) Assignee: Colorado Seminary, which owns and operates The University of Denver, Denver, CO (US)

( * ) Notice: Subject to any disclaimer, the term of this patent is extended or adjusted under 35 U.S.C. 154(b) by 739 days.

This patent is subject to a terminal disclaimer.

(21) Appl. No.: 12/672,105

(22) PCT Filed: Aug. 20, 2008

(86) PCT No.: PCT/US2008/073637
§ 371 (c)(1),
(2), (4) Date: Feb. 8, 2011

(87) PCT Pub. No.: WO2009/026313
PCT Pub. Date: Feb. 26, 2009

(65) Prior Publication Data
US 2011/0117667 A1    May 19, 2011

Related U.S. Application Data

(60) Provisional application No. 60/965,487, filed on Aug. 20, 2007.

(51) Int. Cl.
*G01N 21/76* (2006.01)
(52) U.S. Cl.
CPC ........................ *G01N 21/76* (2013.01)
USPC ................. 436/172; 506/7; 506/13
(58) Field of Classification Search
None
See application file for complete search history.

(56) References Cited

U.S. PATENT DOCUMENTS 5,310,618 A    5/1994   Kawamura
5,532,138 A    7/1996   Singh et al.
(Continued)

FOREIGN PATENT DOCUMENTS

WO    WO 2004/074300    9/2004
WO    WO 2005/024386    3/2005
(Continued)

OTHER PUBLICATIONS

Li, Z. et al., Anomalous C—C bond cleavage in sulfur-centered cation radicals containing a vicinal hydroxy group, 2003, Journal of Organic Chemistry, vol. 68, pp. 8236-8239.*

(Continued)

*Primary Examiner* — Robert Xu
(74) *Attorney, Agent, or Firm* — Lathrop & Gage LLP

(57) ABSTRACT

Provided is a photoamplified fluorescence turn-off assay where a masked photosensitizer is mixed with a fluorescent molecule. This mixture is brightly fluorescent because the masked photosensitizer is not capable of quenching the fluorophore. When the photosensitizer is released and amplified, the photosensitizer quenches the emission of fluorophores very efficiently.

17 Claims, 14 Drawing Sheets

(56) References Cited

U.S. PATENT DOCUMENTS

| | | | |
|---|---|---|---|
| 5,604,104 | A | 2/1997 | Giese et al. |
| 5,739,386 | A | 4/1998 | Holmes |
| 5,767,288 | A | 6/1998 | Rock et al. |
| 5,807,675 | A | 9/1998 | Davalian et al. |
| 5,811,311 | A | 9/1998 | Singh et al. |
| 6,147,205 | A | 11/2000 | McGall et al. |
| 6,180,354 | B1 | 1/2001 | Singh et al. |
| 6,340,599 | B1 | 1/2002 | Singh et al. |
| 6,406,667 | B1 | 6/2002 | Singh et al. |
| 6,472,541 | B2 | 10/2002 | Tsien et al. |
| 6,514,700 | B1 | 2/2003 | Singh |
| 6,627,400 | B1 | 9/2003 | Singh et al. |
| 6,649,351 | B2 | 11/2003 | Matray et al. |
| 6,686,152 | B2 | 2/2004 | Singh et al. |
| 6,692,975 | B2 | 2/2004 | Singh et al. |
| 6,703,248 | B1 | 3/2004 | Singh et al. |
| 6,770,439 | B2 | 8/2004 | Singh et al. |
| 6,818,399 | B2 | 11/2004 | Singh et al. |
| 6,881,836 | B2 | 4/2005 | McGall et al. |
| 2002/0182601 | A1 | 12/2002 | Sampson et al. |
| 2003/0022093 | A1 | 1/2003 | Takahashi |
| 2003/0119008 | A1 | 6/2003 | Fodor et al. |
| 2003/0119059 | A1 | 6/2003 | Still et al. |
| 2003/0170915 | A1 | 9/2003 | Singh et al. |
| 2004/0175696 | A1 | 9/2004 | Ullman et al. |
| 2004/0175741 | A1 | 9/2004 | Buhler et al. |
| 2004/0241711 | A1 | 12/2004 | Singh et al. |
| 2005/0048553 | A1 | 3/2005 | Chenna et al. |
| 2005/0079529 | A1 | 4/2005 | Fodor et al. |
| 2005/0094147 | A1 | 5/2005 | Yaroslavsky et al. |
| 2005/0101765 | A1 | 5/2005 | Barone et al. |
| 2008/0312092 | A1 | 12/2008 | Kutateladze et al. |
| 2009/0247420 | A1 | 10/2009 | Kutateladze et al. |

FOREIGN PATENT DOCUMENTS

| | | |
|---|---|---|
| WO | WO 2007/008471 | 1/2007 |
| WO | WO 2007/008472 | 1/2007 |
| WO | WO 2007/070761 | 6/2007 |
| WO | WO 2009/026313 | 2/2009 |

OTHER PUBLICATIONS

Åkerblom et al. (1998) "Six New Photolabile Linkers for Solid-Phase Synthesis. 1. Methods of Preparationfg," *Mol. Divers.* 3:137-148.

Åkerblom, E.B. (1999) "Six Photolabile Linkers for Solid-Phase Synthesis. 2. Coupling of Various Building Blocks and Photolytic Cleavage," *Mol. Divers.* 4:53-69.

Barnhurst et al. (2001) "Synthesis and Liquid Membrane Transport Properties of Photolabile Molecular Clips Based on Dithiane-Spiro-Crown Ethers," *Org. Lett.*3(17):2633-2635.

Barnhurst et al. (Web Release Feb. 24, 2000) "Efficient Electrochemical Deportation of Carboxylic and Amino Acids from Their 2-(Hydroxymethyl)-1,3-Dithiane (Dim) Esters," *Org. Lett.* 2(6):799-801.

Bawdekar et al. (1966) "Terpenoids LXXXIX Absolute Configuration of Parthenolide," *Tetrahedron Lett.* 11:1225-1227.

Beloglazkina et al. (Web Release Jan. 22, 2007) "Bis-(40(2-Pyridylemethyleneiminophenyl)disulfide—A Chelating Ligand Capable of Self Assembly on Gold Surface and its Complexes with M(BF$_4$ )$_2$and M(ClO$_4$)$_2$; M==Co, Cu and Ni. Experimental and Theoretical Study," *Thin Solid Films* 515:4649-4661.

Borgulya et al. (1984) "Rearrangement of Derivatives of 1,3-Dithiane-5-Amine into Bicyclic 2-Thiazolidines. Crystal Structures of Cis- and Trans-1-(2-Aryl-1,3-Dithian-5-yl)-2-Thiazolidines. Crystal Structures of Cis- and Trans-1-(2-Aryl-1,3-Dithian-5-yl)-2-Thioureas and Cis- and Trans-Aryl-3-imino-7,7a-Dihydro-1H,3H,5H-Thiazolo[3,4-c]Thiazoles," *Helv. Chim. Acta.* 67:1827-1842.

Braslaysky et al. (2007) "Glossary of Terms Used in Photochemistry," 3$^{rd}$ edition, *Pure Appl. Chem.* 79(3):293-465.

Brenner et al. (Jun. 1992) "Encoded Combinatorial Chemistry," *Proc. Nat. Acad. Sci. USA* 89:5381-5383.

Brown et al. (1981) "Location and Orientation Relative to the Micelle Surface for Glucagon in Mixed Micelles with Dodecylphosphocholine," *Biochim. Biophys. Acta* 642:296-312.

Brunecky et al. (2005) "Investigation of the Binding Geometry of a Peripheral Membrane Protein," *Biochemistry* 44:16064-16071.

Bucher et al. (1977) "A 1 MW P-Terphenyl Dye Laser," *Applied Physics* 13:267-269.

Chang et al. (1988) "Molecular Recognition of Biologically Interesting Substrates: Synthesis of an Artificial Receptor for Barbiturates Employing Six Hydrogen Bonds," *J. Am. Chem. Soc.*110:1318-1319.

Ci et al. (1987) "Photochemical Dehydrofragmentation Reactions: Importance of Donor and Acceptor Structure in Determination of Reactivity in Radical Ion Pairs formed in Electron Transfer Photoreactions," *J. Am. Chem. Soc.* 109:7215-7217.

Ci et al. (1989) "Photofragmentation via Single-Electron Transfer: Selective Labilization of Carbon-Carbon Bonds in Amino Alcohols with Several Bonds Between Heteroatom Substituents," *J. Am. Chem. Soc.* 111:3459-3461.

Conn et al. (1997) "Self-Assembling Capsules," *Chem. Rev.* 97(5):1647-1668.

Dale et al. (1992) "Reactivity of Neopentyl-Like Compounds in the Synthesis of Branched Polyethers," *Acta Chem. Scand.* 46(3):278-282.

Esnault et al. (2001) "New Highly Hydrophobic Lewis X Glycolipids: Synthesis and Nonlayer Behavior," *Eur. J. Org. Chem.* 2:253-260.

Ezhov et al. (Jun.-Aug. 2008) "Photolabile Amphiphiles with Fluorogenic Thioxanthone-Dithiane Functionality: Synthesis and Photoinduced Fragmentation in Micelles," *J. Sulfur Chem.* 29(3-4):389-400.

Franz et al. (Jan. 18, 2003) "High-Throughput One-Bead-One-Compound Approach to Peptide-Encoded Combinatorial Libraries MALDI-MS Analysis of Single TentaGel Beads," *J. Comb. Chem.* 5(2):125-137.

Fukunaga et al. (1972) "Alkylation of 1,3,5-Trithianes," *Chem. Lett.* (1):55-58.

Furuta, Toshiaki, et al. Brominated 7-hydroxycoumarin-4-ylmethyls: Photolabile protecting group with biologically useful cross-sections for two photon photo;ysis, 1999, Proceedings of the National Academy of Sciences, USA, vol. 96, p. 1193-1200.

Gaillard et al. (1996) "Photoinduced Electron Transfer Bond Fragmentations," *Acc. Chem. Res.* 29(6):292-297.

George et al. (2005) "Urea and Thiourea Derivatives as Low Molecular-Mass Organogelators," *Chem. Eur. J.* 11(11):3243-3254.

George et al. (Aug. 2006) "Molecular Organogels. Soft Matter Comprised of Low-Molecular-Mass Organic Gelators and Organic Liquids," *Acc. Chem. Res.*39(8):489-497.

George et al. (Web Release May 17, 2006) "Molecular Organogels. Soft Matter Comprised of Low-Molecular-Mass Organic Gelators and Organic Liquids," *Acc. Chem. Res.* 39(8):489-467.

Gustafson et al. (2006) "Externally Sensitized Mesolytic Fragmentations in Dithiane-Ketone Adducts," *Tetrahedron* 62:6574-6580.

Gyenes et al. (Apr. 14, 1998) "Convenient Access to Primary Amines by Employing the Barbier-Type Reaction of N-(Trimethylsilyl)imines Derived from Aromatic and Alipathic Aldehydes," *J. Org. Chem.* 63:2824-2828.

He et al. (Web Release Feb. 2, 2009) "Membrane Insertion of the FYVE Domain is Modulated by pH," *Proteins* 76(4):852-860.

International Search Report and Written Opinion Corresponding to International Application No. PCT/06/25812, Mailed Aug. 10, 2007.

International Search Report and Written Opinion Corresponding to International Application No. PCT/US06/25815, Mailed Mar. 28, 2008.

International Search Report and Written Opinion Corresponding to International Application No. PCT/US2006/061728, Mailed Feb. 1, 2008.

International Search Report and Written Opinion, Corresponding to International Application No. PCT/US08/73637, Mailed Nov. 7, 2008.

(56) References Cited

OTHER PUBLICATIONS

Juaristi et al. (1989) "The Existence of Second-Row Anomeric Interactions. Conformational Analysis of 2-Substituted 5-Methyl-5-aza-1,3-Dithiacyclohexanes," *J. Am. Chem. Soc.* 111(17):6745-6749.

Kim et al. (Sep. 1996) "Dendrimer-Supported Combinatorial Chemistry," *Proc. Nat. Acad. Sci. USA* 93:10012-10017.

Kita et al. (1997) "Molecular Design of C-Pivot Tripodal Ligands: Importance of the Glycerol Structure for Effective Complexation Toward Alkali Metal Cations," *J. Org. Chem.* 62(23):8076-8081.

Kolb et al. (2001) "Click Chemistry: Diverse Chemical Function from a Fewe Good Reactions," *Angew. Chem. Int. Ed.* 40:2004-2021.

Kottani et al. (2006) "Direct Screening of Solution Phase Combinatorial Libraries Encoded with Externally Sensitized Photolabile Tags," *Proc. Nat. Acad. Sci. USA* 103:139(38)13917-13912.

Kottani et al. (2006) "Photoinduced Signal Amplification Through Controlled Externally Sensitized Fragmentation in Masked Sensitizers," *J. Am. Chem. Soc.* 128(46):14794-14795.

Krafft et al. (1988) "Photoactivable Fluorophores. 3. Synthesis and Photoactivation of Fluorogenic Difunctionalized Fuoresceins," *J. Am. Chem. Soc.* 110(1):301-303.

Kurchan et al. (2004) "Dithane and Trithane-Based Photocleavable Systems for Molecular Assembly and Disassembly," *Spectrum* 17(4):20-25.

Kurchan et al. (Web Release Nov. 11, 2004) "Dithiane and Trithiane-Based Photolabile Molecular Linkers Equipped with Amino-Functionality: Synthesis and Quantum Yields of Fragmentation," *J. Photochem. Photobiol. A Chem.* 171:121-129.

Kurchan et al. (Web Release Oct. 19, 2002) "Amino Acid-Based Dithiazines: Synthesis and Photofragmentation of Their Benzaldehyde Adducts," *Org. Lett.* 4(23):4129-4131.

Kutateladze et al. (2005) "Dithane, Trithiane, and Dithiazane-Based Photolabile Scaffolds for Molecular Recognition: Mechanism and Efficiency of the Photoinduced Fragmentation in Aqueous Reductive Environments," *Phosphorus Sulfur Silicon* 180:1379-1384.

Kutateladze et al. (2005) "Toward Parameterization of Spin-Orbit Coupling in Triplet Organic Diradicals Separated by a Partially CONjugated Spacer," *ARKIVOC* (iv):88-101.

Kutateladze et al. (Jan. 2001) "Determination of the Position of the Conformational Equilibrium of a Trans 1,2-Disubstituted Cyclohexane by NMR Spectroscopy," *J. Chem. Education* 78(1):81-82.

Kutateladze et al. (Jan. 23, 2004) "Multivalent Mechanism of Membrane Insertion by the FYVE Domain," *J. Biol. Chem.* 279(4):3050-3057.

Kutateladze et al. (Web Release Aug. 31, 2001) "Conformational Analysis of Singlet-Tripplet State Mixing in Paternò-Büchi Diradicals," *J. Am. Chem. Soc.* 123(38):9279-9282.

Kutateladze, A.G. (2003) "Observations from the XXI$^{st}$ International Conference on Photothemistry(ICP21)," Nara, Japan,I-APS Newsletter, Jul. 26-31, 2003, :11-15.

Lacey et al. (Web Release Oct. 25, 2001) "$^1$H NMR Characterization o fthe Product from Single Solid-Phase Resin Beads Using Capillary NMR Flow Probes," *J. Magn. Res.* 153:215-222.

Lakkakula et al. (Web Release Feb. 10, 2007) "Photoactive Barbiturate Receptors: An Ultimate Lock-and-Key System in Which the Key Unlocks the Lock," *Org. Lett.* 9(6):1077-1079.

Larock et al. (1989) "5. From Azides," In; *Comprehensive Organic Transformations,* VCH Publishers Inc., pp. 409-410.

Lee et al. (1999) "Studies on a Dithiane-Protected Benzoin Photolabile Safety Catch Linker for Solid-Phase Synthesis," *J. Org. Chem.* 64:3454-3460.

Li et al. (2003) "Anomalous C—C Bond Cleavage in Sulfur-Centered Cation Radicals Containing a Vicinal Hydroxy Group," *J. Org. Chem.* 68(21):8236-8239.

Li et al. (2003) "Dithane-Based Photolabile Amphiphiles: Toward Photolabile Liposomes," *Langmuir* 19:6381-6391.

Li et al. (2003) "Photolabile Calixarebe-Based Rosette," *Can J. Chem.* 81:807-810.

Li et al. (Web Release Mar. 20, 2004) "Addition of Lithiated 5-Hydroxymethyl-1,3-Dlthane to Benzaldehyde: HMPA-Controlled Trans Stereoselectivity," *Org. Lett.* 6(8):1213-1216.

Link et al. (2004) "Presentation and Detection of Azide Functionality in Bacterial Cell Surface Proteins," *J. Am. Chem. Soc.* 126(34):10598-10602.

Liu et al. (2002) "A Novel Peptide-Based Encoding System for 'One-Bead One Compound' Peptidomimetic and Small Molecule Combinatorial Libraries," *J. Am. Chem. Soc.* 124(26):7678-7680.

Majjigapu et al. (2005) "Release and Report: A New Photolabile Caging System with a Two-Photon Fluorescence Reporting Function," *J. Am. Chem. Soc.* 127(36):12458-12459.

Majjigapu et al. (2007) "Photoamplification and Multiple Tag Release in a Linear Peptide-Based Array of Dithiane Adducts," *Angew. Chem.* 46(32):6137-6140.

Martins et al. (Web Release Mar. 17, 2001) "Unprecedented Sigmatropic Rearrangements Leading to 2,3-Dihydro-1$H$-2-benzazepine-3-carboxylic Acid," *J. Org. Chem.* 66(8):2884-2886.

McHale et al. (Web Release Dec. 1998) "An Efficient Photo-SET-Induced Cleavage of Dithiane-Carbonyl Adducts and Its Relevance to the Development of Photoremovable Protecting Groups for Ketones and Aldehydes," *J. Org. Chem.* 63(26):9924-9931.

Mitkin et al. (2001) "Synthesis of Dithiane-Based Photolabile Molecular Systems," *Synthesis* :1133-1142.

Mitkin et al. (Web Release May 15, 2001) "Dithiane- and Trithiane-Based Photolabile Scaffolds for Molecular Recognition," *Org. Lett.* 3(12):1841-1844.

Moerner et al. (Jul. 29, 2004) "Single-Photon Sources Based on Single Molecules in Solids," *New J. Phys.* 6(88):1-21.

Mohmeyer et al. (2006) "An Efficient Organogelator for Ionic Liquids to Prepare Stable Quasi-Solid-State Dye-Sensitized Solar Cells," *J. Mater. Chem.* 16(29):2978-2983.

Nestler et al. (1994) "A General Method for Molecular Tagging of Encoded Combinatorial Chemistry Libraries," *J. Org. Chem.* 59(17):4723-4724.

Nijegorodov et al. (Mar. 2000) "Systematic Investigation of Adsorption, Fluorescence and Laser Properties of Some *p*- and *m*-oligophenylenes," *Spectrochim. Acta A* 56(4):783-795.

Nilsson et al. (Web Release Jun. 9, 2000) "Staudinger Ligation: A Peptide from a Thioester and Azide," *Org. lett.* 2(13):1939-1941.

Nishi et al. (Web Release Mar. 15, 2006) "Wide Electrochemical Window at the Interface Between Water and a Hydrophobic Room-Temperature Ionic Liquid of Tetrakis[3,5-bis(Trifluoromethyl)phenyl]borate," *Anal. Chem.* 78(8):2726-2731.

Ohlmeyer et al. (Dec. 1993) "Complex Synthetic Chemical Libraries Indexed with Molecular Tags," *Proc. Nat. Acad. Sci. USA* 90:10922-10926.

Oppolzer et al. (1994) "Asymmetric Alkylations of a Sultam-Derived Glycine Equivalent: Practical Preparation of Enantiomerically Pure α-Amino Acids," *Helv. Chim. Acta* 77(8):2363-2380.

Pellois et al. (2004) "Simultaneous Triggering of Protein Activity and Fluorescence," *J. Am. Chem. Soc.* 126(23):7170-7171.

Qiu et al. (Sep. 19, 2006) "Protein Surface Hydration Mapped by Site-Specific Mutations," *Proc. Nat. Acad. Sci. USA* 103(38):13979-13984.

Rebek, J., Jr. (Web Release Dec. 10, 1998) "Reversible Encapsulation and Its Consequences in Solution," *Acc. Chem. Res.* 32(4):278-286.

Routledge et al. (Feb. 17, 1997) "The Use of a Dithiane-Protected Benzoin Photolabile Safety Catch Linker for Solid-Phase Synthesis," *Tetrahedron Lett.* 38(7):1227-1230.

Salvatore et al. (Web Release Jan. 12, 2002) "Cesium Effect : High Chemoselectivity n Direct N-Alkylation of Amines," *J. Org. Chem.* 67(3):674-683.

Sarkar et al. (1996) "An NMR Method to Identify Nondestructively Chemical Compounds Bound to a Single Solid-Phase-Synthesis Bead for Combinatorial Chemistry Applications," *J. Am. Chem. Soc.* 118(9):2305-2306.

Saxon et al. (Mar. 17, 2000) "Cell Surface Engineering by a Modified Staudinger Reaction," *Science* 287:2007-2010.

Saxon et al. (Web Release Jun. 20, 2000) "A 'Traceless' Staudinger Ligation for the Chemoselective Synthesis of Amide Bonds," *Org. Lett.* 2(14):2141-2143.

(56) References Cited

OTHER PUBLICATIONS

Schoevaars et al. (1997) "Toward a Switchable Molecular Rotor. Unexpected Dynamic Behavior of Functionalized Overcrowded Alkenes," *J. Org. Chem.* 62(15):4943-4948.

Seidel et al. (Web Release Jun. 21, 2002) "High-Symmetry Coordination Cages via Self-Assembly," *Acc. Chem. Res.* 35(11):972-983.

Valiulin et al. (2008) "Effect of β-Alkylthioethyl Substitution in 1,3-Dithianes: Quasianchimeric Assistance in Photoinduced Electron Transfer," *J. Org. Chem.* 73:6393-6396.

Valiulin et al. (2009) "A Peculiar Quenching Concentration Dependence of Photoinduced Fragmentation in Dithiane-Carbonyl Adduct: A Mechanistic Experimental and Theoretical Study," *J. Photochem. Photobiol. A, Chem.* 206:80-86.

Valiulin et al. (Web Release Apr. 3, 2009) "Effect of Intramolecular Paternò-Büchi Reaction on the Thermodynamics and Kinetics of Nearly Degenerate [3,3](9):-Sigmatropic Shift in Fluxional Polycycles," *J. Org. Chem.* 74:3484-3490.

Valiulin et al. (Web Release Aug. 30, 2007) "Interrupted Oligomerization Revisited: Simple and Efficient One-Pot Multicomponent Approach to Versatile Synthetic Intermediates," *Org. Lett.* 9(20):4061-4063.

Valiulin et al. (Web Release Dec. 11, 2007) "2,6,7-Trithiabicyclo[2.2.2]Octanes as Promising Photolabile Tags Combinatorial Encoding," *J. Org. Chem.* 73(1):335-338.

Valiulin et al. (Web Release May 26, 2006) "When Ethyl Is Infinitely Different from Methyl: Double Addition of Lithiated Dithianes to Aromatic Carboxylates Revisited," *J. Org. Chem.* 71(13):5047-5049.

Vath et al. (Web Release Mar. 24, 2001) "Photoinduced C—C Bond Cleavage in Dithiane-Carbonyl Adducts: A Laser Flash Photolysis Study," *J. Org. Chem.* 66(8):2887-2890.

Vazquez et al. (2003) "Fluorescent Caged Phosphoserine Peptides as Probes to Investigae Phosphorylation-Dependent Protein Associations," *J. Am. Chem. Soc.* 125(34):10150-10151.

Veldhuyzen et al. (2003) "A Light-Activated Probe of Intracellular Protein Kinase Activity," *J. Am. Chem. Soc.* 125:13358-13359.

Vieira et al. (Web Release Jan. 13, 2007) "Photoinduced Electron-Transfer Reactions in Two Room-Temperature Ionic Liquids: 1-Butyl-3-Methylimidazolium Hexafluorophisphate and 1-Octyl-3-Methylimidazolium Hexafluorophosphate," *J. Chem. Phys. B* 111(18):5023-5029.

Wade et al. (Web Release Oct. 5, 2006) "Conformational Analysis of Spiro-bis-dithiepins: A Peculiar Case of Axial Chirality," *Org. Lett.* 8(22):5121-5124.

Wadhawan et al. (2003) "Electrocatalytic Reactions Mediated by N,N,N',N'-Tertraalkyl-1,4-Ohenylenediamine Redox Liquid Microdroplet-Modified Electrodes: Chemical and Photochemical Reactions in, and At the Surface of Femtoliter Droplets," *J. Am. Chem. Soc.* 125(37):11418-11429.

Wagner et al. (1973) "Effects of Ring Substituents on the Type II Photoreactions of Phenyl Ketones. How Interactions Between Nearby Excited Triplets Affects Chemical Reactivity," *J. Am. Chem. Soc.* 95(17):5604-5614.

Wan et al. (2001) "Photoinduced 1,3-Proton Shift in Methyldithiepines as a Potential Way of Modulating Hyperpolarizabilities," *J. Org. Chem.* 66(5):1894-1899.

Wan et al. (2002) "Liposomes from Novel Photolabile Phospholipids: Light-Induced Unloading of Small Molecules as Monitored by PFG NMR," *J. Am. Chem. Soc.* 124(20):5610-5611.

Wan et al. (Aug. 25, 1999) "Photooxidation of Methyldithiepines into Dithiepin Carboxaldehydes in Carbon Tetrachloride," *Org. Chem.* 1(6):937-939.

Wan et al. (Web Release Mar. 24, 2000) "Direct Transformation of 1,3-Dihalides into Dithiepins Via a Novel One Pot Reaction with Carbon Disulfide and Sodium Borohydride," *Org. Lett.* 2(8):1133-1135.

Wan et al. (Web Release Nov. 10, 2000) "Molecular Assembly and Disassembly: Novel Photolabile Molecular Hosts," *Org. Lett.* 2(24):3817-3819.

Zhao et al. (2004) "New Caged Coumarin Fluorophores with Extraordinary Uncaging Cross Sections Suitable for Biological Imaging Applications," *J. Am. Chem. Soc.* 126:4653-4663.

\* cited by examiner

PHOTOINDUCED SIGNAL AMPLIFICATION THROUGH EXTERNALLY SENSITIZED PHOTOFRAGMENTATION IN MASKED PHOTOSENSITIZERS AND PHOTOAMPLIFIED FLUORESCENCE TURN-OFF SYSTEM

STATEMENT REGARDING FEDERALLY SPONSORED RESEARCH OR DEVELOPMENT

This invention was made with government support under CHE-314344 and CHE-640838 awarded by NSF and GM067655 awarded by NIH. The United States government has certain rights in the invention.

CROSS-REFERENCE TO RELATED APPLICATIONS

This application is the U.S. National Stage of International Application No. PCT/US2008/073637, filed Aug. 20, 2008, which claims the benefit of U.S. provisional application Ser. No. 60/965,487, filed Aug. 20, 2007, both of which are incorporated by reference in its entirety to the extent not inconsistent with the disclosure herewith.

BACKGROUND OF THE INVENTION

The detection of small quantities of materials or amplification of the signals related to the study of interactions between small quantities of materials, i.e., between ligands and receptors is important in developing and using analytical assays and screening assays, among other uses. Current methods used to study small quantities of materials suffer from many disadvantages, including difficulty in isolating and detecting targeted compounds.

An improved method for detecting small amounts of molecules of interest is needed.

SUMMARY OF THE INVENTION

Provided are methods and systems that take advantage of the amplification of signals associated with photochemically induced fragmentation of masked sensitizers. More specifically, provided is a method of photochemically amplifying the chemical signal associated with unmasking a photosensitizer and releasing a radical leaving group when a photochemical chain reaction is initiated by a reaction photosensitizer. More specifically, the photosensitizer is masked via the formation of a covalent bond between the photosensitizer and a masking group that disrupts conjugation of the photosensitizer. A free (unmasked) reaction photosensitizer is placed in releasing proximity to the masked photosensitizer and irradiated at a wavelength the reaction photosensitizer absorbs. This causes the masked photosensitizer to release the masking group as a radical leaving group, regenerating the photosensitizer. The release of the masking group from masked photosensitizer molecules continues as long as masked photosensitizer molecules are in releasing proximity to the reaction photosensitizer or unmasked photosensitizer, until a side reaction occurs which stops the chain propagation, or until the source of photoradiation is turned off. The amount of departing masking group is "amplified" and can be detected.

In one embodiment, a fluorescence "turn off" assay is provided. We have discovered that an amplified sensitizer can quench the fluorescence of a fluorophore and that the fluorescence quenching associated with the amplification of release of unmasked sensitizer can be sensitively detected. This is useful for bioanalytical applications, where a small amount of initial sensitizer tethered to an analyte can trigger an amplified quenching effect on fluorophore allowing for the detection of minute amounts of this analyte. Extremely low detection limits (e.g., $10^{-8}$ M) have been achieved, however, there is no theoretical limit to how low such detection limit can be.

In another embodiment, engineering spatially compartmentalized arrays with the use of physically constrained solvents, such as gelated solvents is provided. Compartmentalization allows for free 3-dimensional collisional quenching in the solution while providing structural elements which are useful for fabrication of pixilated spatially addressable arrays, such as arrays on a chip.

In another embodiment, the problem of fast solvent evaporation from the chip is solved by the use of high boiling point liquids and ionic liquids. The ionic liquids can be gelated, as described herein.

In another embodiment membranes of anodized aluminum (for example Anodisc) are loaded with solvents or organogels or ionic liquids to provide nano-scale compartmentalization for ultra-high density 2-dimensional arrays.

In another embodiment microcapillary array plates (for example Schott) are loaded with solvents or organogels or ionic liquids to provide micro-scale compartmentalization for high density 2-dimensional arrays, which can be imaged directly by CCD, CMOS or other imaging devices without additional optics.

One embodiment of a reaction photosensitizer is an electron-transfer photosensitizer. It is to be understood that any sensitizer can be used as long as the fragmentation/unmasking reaction is sensitized by the reaction photosensitizer. For example, energy transfer sensitizers can be used. Therefore, whenever the term "electron-transfer photosensitizer" is used herein, it is to be understood that any type of sensitizer can be substituted, as long as the fragmentation/unmasking reaction is sensitized by the sensitizer. When the term "reaction photosensitizer" is used herein, it is intended that all types of sensitizers that can be used in the invention are collectively and individually disclosed.

More specifically, provided is a method of photoinduced signal amplification comprising: providing a plurality of masked photosensitizers, each masked photosensitizer having a masking group bonded to a photosensitizer through a releasable covalent bond which disrupts the conjugation of the photosensitizer; providing a reaction photosensitizer in releasing proximity to a first masked photosensitizer; exciting the reaction photosensitizer with photoradiation, whereby the reaction photosensitizer induces release of the masking group from the first masked photosensitizer, producing a first unmasked photosensitizer which, in turn, induces release of the masking group from a second masked photosensitizer in releasing proximity to the first masked photosensitizer, and so on. The members of a specific binding pair can be attached to the masked photosensitizer and/or reaction photosensitizer, using methods known in the art and described herein. One embodiment of the invention further comprises: providing a first member of a specific binding pair in releasing proximity to a masked photosensitizer; and in specific binding proximity to a second member of a specific binding pair which is attached to the reaction photosensitizer, whereby the members of the specific binding pair bind prior to or coincident with excitation of the reaction photosensitizer. The specific binding pair may be a ligand-receptor pair. In one embodiment, the photosensitizer is a fluorescent molecule. In one embodiment of the invention at least one masked photosensitizer has a first member of a specific binding pair attached thereto, and the electron-transfer photosensitizer has a second member of a specific binding pair attached thereto. In one embodiment of the invention, the plurality of masked photosensitizers is attached to a support. The support can be a dendrimer, particle, surface or liposome, for example. The surface is selected from the group consisting of: conductive, semi-conductive, or non-conductive. In one embodiment of the invention at least one of the plurality of photosensitizers is attached to a first member of a ligand-receptor pair and the reaction photosensitizer is attached to the second member of a ligand-receptor pair. The masking group is a member of the group consisting of: dithiane, trithiane, dithiazine, tert-alkyl, nitrile, carboxamide, and other radical leaving groups. In one embodiment, the reaction photosensitizer is an electron-transfer photosensitizer.

Also provided is a library of support-bound molecules comprising: a plurality of spatially separated groups of masked photosensitizers bound to a support, each group comprising a plurality of masked photosensitizers, each masked photosensitizer having a masking group bonded to a photosensitizer through a releasable covalent bond which disrupts the conjugation of the photosensitizer, said masked photosensitizers in each group in releasing proximity with each other. The support can be a flat support. Each group may be bound to a different spherical support, such as a particle.

Also provided is a method of making dendrimers "universally" soluble in aqueous solutions, including buffer solutions, regardless of what kinds of ligands/tags are immobilized on them. The use of dendrimers in biological applications has been limited by the difficulty in solubilizing the dendrimers in aqueous solutions, including buffer solutions. This method comprises providing a solubilizing medium (for example, detergents, such as sodium dodecyl sulfate (SDS) or phosphocholines), to incorporate the dendrimers into micelles. The dendrimers are used in the photo-amplification reactions described herein. This method provides solubility in aqueous solutions and spatial separation of photoamplification chemistry from the molecular recognition chemistry, i.e. the ligands for molecular recognition (or other uses as described herein and as known in the art) are exposed into the aqueous solution, while the photoamplification occurs within the hydrophobic environment of the micelles, improving quantum yields and not interfering with the recognition chemistry. The applications of this method are apparent to one of ordinary skill in the art using the disclosure herein.

Another aspect of the invention is a kit for conducting an assay for an analyte. The kit comprises, in package combination, a support having spatially separated groups of masked photosensitizers bound thereto, each group comprising a plurality of masked photosensitizers having a first member of a specific binding pair bound thereto through a releasable covalent bond. At least one of the groups is capable of binding to the second member of the specific binding pair (analyte). The spatially separated groups may be arranged in any convenient manner on the support. For example, the groups may be arranged in horizontal or vertical rows on the support, each row being one or more molecules wide and one or more molecules long. The groups may be arranged in circular "dots" on the support, where each dot is spatially separated from the others on the support.

As used herein, a "fluorophor" is a molecule or fragment that exhibits detectable fluorescence. It is preferable that the fluorophor excitation spectrum is different than the photosensitizer absorption spectrum so that exciting the sensitizer will not also excite the fluorophor.

As used herein, a "quenching photosensitizer" is a molecule of portion thereof which is capable of reducing the fluorescence emission intensity of a fluorophor.

As used herein, "quenching proximity" means a fluorescent molecule and a quenching molecule or fragment are close enough physically so that the quenching molecule reduces the fluorescence intensity of the fluorescent molecule.

As used herein, "spatially separated" refers to the separation required to prevent the extent of reaction between groups that would prevent the desired outcome of the invention. The degree of required spatial separation between groups is easily determined by routine experiments that do not involve undue experimentation, or may be calculated using well-known equations.

As used herein, "photosensitizer" is a molecule that absorbs light and passes its energy to another substance which then reacts. Photosensitizers useful in the invention to be masked contain, or can be modified to contain, at least one conjugated bond system that is disrupted by covalent bonding of the masking group(s). As used herein, "masked photosensitizer" is a photosensitizer molecule whose conjugation has been disrupted by the attachment of a masking group, so that the absorbance spectrum of the masked photosensitizer is shifted to the blue spectrum (shorter wavelength) than an unmasked photosensitizer. As used herein, "releasing proximity" between masked photosensitizers indicates the photosensitizers are at an appropriate distance apart to allow the desired reaction to occur between the photosensitizers, for example, the cleavage of a releasable covalent bond. As used herein, "specific binding proximity" indicates two groups are capable of specific binding, as defined herein. As used herein, "electron-transfer photosensitizer" is a molecule which can be excited using radiation to an excited state, whereby an electron from the excited state can be transferred to another molecule. Examples of oxidative electron-transfer photosensitizers include benzophenones, xanthones, dicyanonaphthalene, dicyanoanthracene, and other compounds possessing carbonyl-, cyano-, nitro- and other electron withdrawing substituents, as known in the art. Examples of reductive electron-transfer photosensitizers include compounds possessing amino-, sulfido- and other electron donating substituents as known in the art.

As used herein, "specific binding pair member" refers to one of two different molecules which specifically binds to the other molecule. One example of the members of the specific binding pair are ligand and receptor. Other examples of the members of the specific binding pair are members of an immunological pair such as an antigen-antibody, hormone-hormone receptor, and other pairs known in the art. "Ligand" refers to any molecule for which a receptor naturally exists or can be prepared. Any member of a specific binding pair can be modified to include groups that allow binding to the reaction photosensitizer or masked photosensitizer, or other groups for any convenient purpose, as known in the art. "Specific binding" refers to the specific recognition of one of two different molecules for the other compared to less recognition of other molecules. As used herein, "proximal" indicates two groups are located at a distance apart which allows the desired reaction to occur. As used herein, "masking group" is a group, which when bound to a photosensitizer, disrupts the conjugation of the photosensitizer, creating a masked photosensitizer. Examples of masking groups include: dithiane, trithiane, dithiazine, tert-alkyl including tertiary butyl, nitrile, isobutyronitrile, carboxamides, and other groups that form radical leaving groups, as known in the art. As used herein, "releasable covalent bond" is a covalent bond which can be broken by a sensitized exposure to cleaving photoradiation. It is preferred that the "releasable covalent bond" used to mask the photosensitizer is not capable of cleaving upon direct irradiation, since that will lead to an indiscriminant cleavage and release of unmasked phososensitizers, whether or not the unmasked photosensitizers are proximal to the molecule of interest. In the embodiment using an electron-transfer photosensitizer, for example, it is preferred that the "releasable covalent bond" is only be cleavable by a stepwise process, in which first, an electron-transfer photosensitizer molecule absorbs light, second, oxidizes the masking group of a masked photosensitizer via electron transfer, and only after that the fragmentation of the releasable covalent bond occurs in the formed cation-radical of the masked photosensitizer molecule. Photoinduced electron transfer-reduction is also included herein.

As used herein, "cleaving photoradiation" or "cleaving wavelength" is light having the appropriate energy (wavelength) to excite an electron-transfer photosensitizer and to enable it to initiate energy or electron transfer resulting in fragmentation of a releasable covalent bond, as known in the art. The appropriate wavelength of cleaving photoradiation is determined by measuring the absorbance spectrum of the masked photosensitizer, as known in the art. Examples of cleaving photoradiation include wavelengths in the ultraviolet spectrum, visible and infrared spectrum (between about 180 nm and 1.5 µm, for example) and all individual values and ranges therein, including UV-A (between about 320 and about 400 nm); UV-B (between about 280 and about 320 nm); and UV-C (between about 200 and about 280 nm). Other useful ranges include the radiation from visible, near-IR and IR lasers (about 500 nm to about 1.5 µm). As used herein, "unmasked photosensitizer" is a photosensitizer from which a masking group has been released. As used herein, "fluorescence" includes phosphorescence. As used herein, "support" or "surface" indicates a material to which a molecule used in the invention can be configured to attach. "Support" or "surface" does not necessarily indicate a substantially flat surface. The support or surface can have any of a number of shapes, such as strip; rod; particle, including bead; and the like. Examples of surfaces include conductive, semi-conductive, and non-conductive, including metal, silicon, ITO, glass and quartz. Conductive surfaces include metal-containing surfaces, or non-metal surfaces with at least a partially electrically conductive layer or portion thereof attached thereto. Examples of electrically conductive materials include metals, such as copper, silver, gold, platinum, palladium, and aluminum; metal oxides, such as platinum oxide, palladium oxide, aluminum oxide, magnesium oxide, titanium oxide, tin oxide, indium tin oxide, molybdenum oxide, tungsten oxide, and ruthenium oxide; and electrically conductive polymeric materials, and mixtures thereof. For certain applications, an electrically conductive material can be deposited on or otherwise applied to a substrate to form a conductive surface. For example, an electrically conductive material can be deposited on a glass substrate or a silicon wafer or a plastic substrate to form a conductive surface. The substrate can be flexible. In other applications, the substrate is itself conductive such as a metal substrate. In some instances, a conductive layer can have a substantially uniform thickness and a substantially flat outer surface. In other instances, a conductive layer can have a variable thickness and a curved, stepped, or jagged outer surface. As used herein, "outer" means the side of the layer that is away from the substrate.

As used herein, a molecule having a "carbonyl group" contains the following structure:

As used herein, a "dendrimer" is a structure formed from regular, highly branched monomers leading to a monodisperse, tree-like or generational structure. Dendrimers are built one monomer layer, or "generation," at a time. A dendrimer comprises a multifunctional core molecule with a dendritic wedge attached to each functional site. The core molecule is referred to as "generation 0." Each successive repeat unit along all branches forms the next generation, "generation 1," "generation 2," and so on until the terminating generation. An example of a dendrimer is the commercially available PAMAM dendrimer (Aldrich Chemical Co. As used herein, a "particle" is a discrete support that can be coated or partially coated with a variety of materials, such as groups having functional groups allowing attachment of molecules. Examples of particles include commercially available particles such as TentaGel beads (Fluka Chemical Co.). As used herein, "liposome" is a fluid-filled structure whose walls are made of layers of phosopholipids. As used herein, "layer" does not necessarily indicate a complete monolayer is formed. There may be one or more gaps or defects in the layer, and there may be more than one monolayer with or without gaps or defects.

As used herein, "molecule" refers to a collection of chemically bound atoms with a characteristic composition. As used herein, a molecule can be neutral or can be electrically charged. The term molecule includes biomolecules, which are molecules that are produced by an organism or are important to a living organism, including, but not limited to, proteins, peptides, lipids, DNA molecules, RNA molecules, oligonucleotides, carbohydrates, polysaccharides, glycoproteins, lipoproteins, sugars and derivatives, variants and complexes and labeled analogs of these. As used herein, "substantially" means more of the given structures have the listed property than do not have the listed property. As used herein, "about" is intended to indicate the value given is not necessarily exact, either as a result of the inherent uncertainty in measurement, or because the values surrounding the value given function in the same way as the value given. As used herein, "attach" refers to a coupling or joining of two or more chemical or physical elements. Examples of attachment includes chemical bonds such as chemisorptive bonds, covalent bonds, ionic bonds, van der Waals bonds, and hydrogen bonds. Various organic solvents and aqueous solutions, and mixtures thereof can be used in the reactions described herein, as known in the art. Additives such as buffers can be used as long as the additives do not prevent the desired reactions from occurring.

It is noted that derivatives of photosensitizers can be made that allow bonding of the desired masking group(s) and other desired groups in view of the disclosure herein and using methods of organic synthesis known in the art. These derivatives are apparent to one of ordinary skill in the art in view of the disclosure herein and these derivatives can be made using art known methods without undue experimentation. The formation of the releasable covalent bond between the masking group and photosensitizer can be before, after, or during attachment of any portion thereof to a support or other structure. Unless otherwise specified, all groups described herein, including photosensitizers, masking groups, reaction photosensitizers, and unmasked photosensitizers can be optionally substituted with various groups, such as groups that allow attachment to another group, groups that allow attachment to a surface, allow alteration of the optical properties of the group, groups that are present in commercially available analogues of groups or are as a result of synthesis methods used, as long as the substitution does not interfere with the desired use. Ring structures can be optionally substituted with one or more halogens, such as fluorine or chlorine. Ring structures can also be substituted with one or more heteroatoms in the ring, for example. Other substituents can be added to various groups including ring structures, such as alkyl groups, alkylene groups, alkenyl groups, alkenylene groups, alkynyl groups, alkynylene groups, aryl groups, arylene groups, iminyl groups, iminylene groups, hydride groups, halo groups, hydroxy groups, alkoxy groups, carboxy groups, thio groups, alkylthio groups, disulfide groups, cyano groups, nitro groups, amino groups, alkylamino groups, dialkylamino groups, silyl groups, and siloxy groups.

DETAILED DESCRIPTION OF THE INVENTION

Figure 1A:
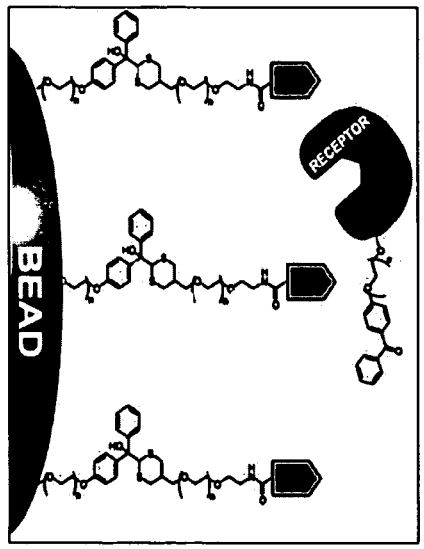
FIG. 1 shows masked photosensitizers bound to a bead (or any other support) with a ligand attached thereto, with receptor bound free photosensitizer (reaction photosensitizer) binding to the ligand, causing chain cleavage. This causes all ligands (or, alternatively, tags encoding this particular bead) from the "winning bead" to be released into solution for detection.

The invention is further described by the following non-limiting description.

The photoinduced fragmentation reaction can occur as a result of a single photon absorption or two photon absorption. The actual wavelength value used depends on the difference of the UV/vis (or near-IR for the two photon cases) absorption maximum of the photosensitizer and the masked photosensitizer. An excitation wavelength in the range that the unmasked photosensitizer absorbs and masked photosensitizer does not absorb to a great extent, is used to prevent exciting the masked photosensitizer and creating competing reactions. For example, substituted benzophenones that absorb light around 350-370 nm can be selectively excited in the presence of the masked photosensitizers, because the masked photosensitizers have absorption maxima below 300 nm.

The actual amplification efficiency depends on the ratio of the extinction coefficients of the free photosensitizer and its masked form. For example, the extinction coefficient of benzophenone at 350 nm is approximately 100 L mol$^{-1}$ cm$^{-1}$. If the masked benzophenone has an extinction coefficient<0.1 L mol$^{-1}$ cm$^{-1}$ at this wavelength, there would be a 1000 fold amplification, for example. Benzene has an extinction coefficient of <1 L mol$^{-1}$ cm$^{-1}$ at 280 nm, which decreases to near zero at wavelengths over 300 nm, indicating that high levels of amplification are possible using the methods of the invention.

Ligand-Receptor Binding

In this example, ligands are immobilized on solid support beads or dendrimers through a tether containing a dithiane-benzophenone adduct (masked photosensitizer). This creates an externally sensitized photolabile linker, which at the same time contains a masked photosensitizer. Beads containing different ligands are created using known techniques, to form a library. Each kind of bead displays an amount of the ligand sufficient for subsequent solution identification of its structure. The receptor is modified by tethering one or more free photosensitizer moieties, e.g. benzophenone, via polyethyleneglycol, or PEG linker (here and below the term "free photosensitizer" implies a tethered benzophenone, not reacted with lithiated dithiane). In the assay, the pool of beads is incubated with a very small amount of the modified receptor, much smaller than the molar amount of the ligand immobilized on one bead. After equilibrating, the suspension is exposed to 350-370 nm irradiation. The photosensitizer brought by the receptor sensitizes dithiane-benzophenone cleavage in the proximal photolabile tethers on the "winning" bead, releasing the lead ligand into solution and liberating more benzophenone (still attached to the bead), which in turn induces fragmentation in the nearby photolabile tethers until, in the ideal limit, the whole bead is trimmed off of the winning ligand. The suspension is centrifuged or filtered and the content of the solution is analyzed using a method appropriate for the given type of ligand, as known in the art. The resulting solution contains the original receptor molecules and "amplified" amounts of the lead compound, still carrying tethered dithiane (which can be detected). Sensitivity of the method depends on the extent of photochemical chain propagation before a nonproductive benzophenone photoreduction or other side reactions interrupt it. The inter-bead sensitization is not of concern, because bimolecular reactions between macroscopic objects are rare due to extremely low collision count. Such reactions may occur in case of sticky beads, but the most commonly used PEG-grafted beads, e.g. TentaGel, are shown not to cluster. The same applies to the PEG-grafted dendrimers.

Figure 1B:
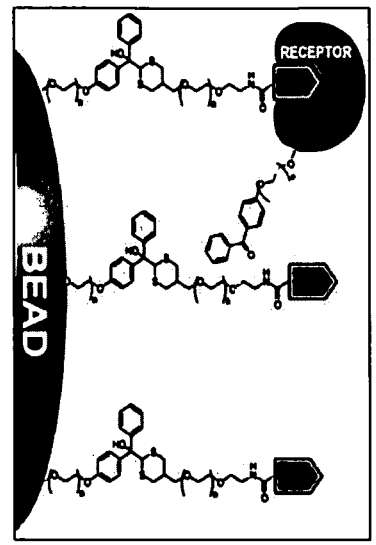
Figure 1C:
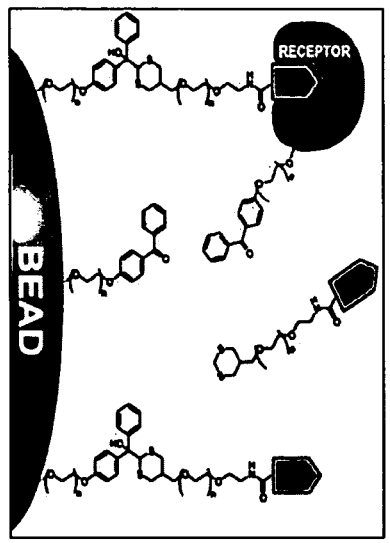
Figure 1D:
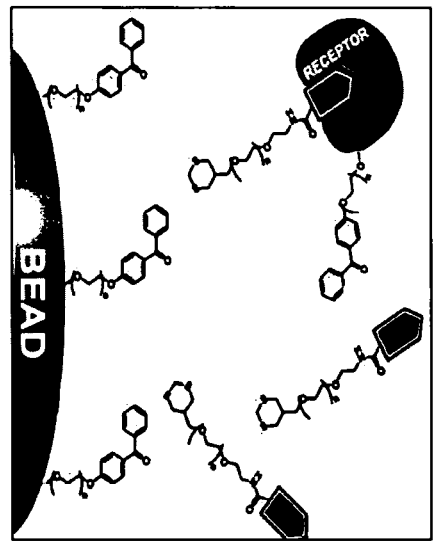

FIG. 1A shows a receptor bearing tethered benzophenone approaching the bead carrying the complementary ligand. FIG. 1B shows binding of the receptor and ligand, bringing benzophenone into the proximity of dithiane-benzophenone photocleavable unit. FIG. 1C and 1D show the sample being irradiated—the first photoinduced cleavage can occur at a neighboring stem or at the stem to which the receptor is bound. In either case the latent benzophenone moiety bound to the bead is unmasked, so it can further sensitize the cleavage of the neighboring photolabile groups and thus carry the "chain".

In addition to amplification, a practical advantage of this approach is that one does not need to sift through dyed or fluorescent beads to select and separate the promising beads mechanically and cleave off the ligand for analysis. In the methods described herein, molecules of interest end up in the bulk solution in sufficiently high concentration for detection as a result of "photo-development" of the beads. Moreover, this approach alleviates problems related to the solid support matrix effects on binding. Since only fractional amount of the receptor is used, it has freedom of binding to the most exposed (and therefore less perturbed) tethered ligands. The ligands less accessible for the receptor need not necessarily be bound to the receptor. They are still released upon irradiation via the propagation of the amplification chain.

These examples are also applicable to the tagged libraries approach [tagged libraries are described in, for example, Brenner, S.; Lerner, R. A. Proc. Natl. Acad. Sci. U.S.A. 1992, 89, 5381-5383]. In this embodiment the tags encoding the individual bead are attached to the masking moiety (e.g. dithiane), whereas the actual ligands are present at the bead surface at much smaller concentration. The recognition and photoamplification, as described above, releases the tags from the beads which contain the ligands which are recognized by the receptor ("winning" beads) into the solution, where they are analyzed by existing analytical methods. As known in the art, the ligand can be attached to the reaction photosensitizer and the receptor can be attached to the masked photosensitizer.

A critical distinction of this invention is that the "winning" particle is identified based on the material released into the solution which is detected. This allows for utilization of dendrimers and other particles for combinatorial screening. There are numerous advantages of dendrimer based libraries [see for example, Kim, R. M; Mahua, M.; Hutchings, S. M.; Griffin, P. R.; Yates, N. A.; Bernick, A. M.; Chapman, K. N. Proc. Natl. Acad. Sci. USA, 1996, 93, 10012-10017]. The single major obstacle in the dendrimer applications for combinatorial libraries is assaying them. Most of the binding assays are based on fluorescence imaging of beads and mechanical isolation of them, followed by analysis. Mechanical separation of a single dendrimer molecule is not practical, hence—the bottleneck. The method of assaying for binding described herein does not require mechanical isolation and therefore is applicable to very small particles or individual molecules.

Dendrimer Solubility

One difficulty in using dendrimers for applications in biological systems is their low solubility in aqueous solutions. It has been discovered that dendrimers can be solubilized in aqueous buffers and other aqueous solutions regardless of what kinds of ligands/tags are immobilized on them by using a solubilizing medium to incorporate the dendrimers into micelles. This gives the dendrimers solubility in aqueous solutions, and spatially separates photoamplification chemistry from the molecular recognition chemistry, i.e. the ligands for molecular recognition are exposed into the aqueous solution, while the photoamplification occurs within the hydrophobic environment of the micelles, improving quantum yields and preventing interference with the recognition chemistry. As used herein, "solubilizing medium" is a medium which allows one or more dendrimers to form one or more micelles. Solubilizing media include detergents, such as sodium dodecyl sulfate (SDS) or phosphocholines, and other substances and mixtures as known in the art.

Detection Limits/Library Loading Math

The technology currently exists to analyze and characterize very small amounts of compounds in combinatorial applications. [for example: single bead NMR analysis: Lacey, M. E; Sweedler, J. V.; Larive, C. K.; Pipe A. J.; Farrant, R. D. *J. Magn. Res.*, 2001, 153, 215-222; single bead MALDI-MS analysis: Franz, A. H.; Liu, R.; Song, A.; Lam, K. S.; Lebrilla, C. B. *J. Comb. Chem.*, 2003, 125-137].

Polypeptide sequencing requires about 5 picomoles of polypeptide (natural amino acids). A typical TentaGel with 90 micron bead size would have 3 million beads per gram with capacity of about 0.1 nmol per one bead. This is 20 times the minimal amount needed for sequencing. If the photochemical amplification is on the order of 100, only picomolar amount of a receptor is needed for binding assays on a million member library, provided the binding constant is large enough for binding to occur at these concentrations. Libraries of synthetic compounds require much larger amounts of ligands for direct structural characterization. However, analytical methods are also becoming available for one-bead characterization. Most notably, mass spectrometry methods and NMR can be used for single bead analysis. Even at the current level of sensitivity, about 50 nanomoles of an unknown can be analyzed by NMR. For the example presented above, at the capacity of 0.1 nmol per bead, this translates into a minimal number of 500 beads carrying the same compound. This, in turn, means that an about 10,000 member library can be presented on 1 g of TentaGel beads with the possibility of direct characterization of the lead compound by NMR. Using a conservative amplification coefficient of 100, one calculates that only 0.5 nmol of the benzophenone-PEG-receptor is needed for the NMR assay.

With GC-MS based detection of the dithiane tags the detection limit is much lower. For example, using a 10 year old vintage HP GC-MS chromatograph six model tags were able to be quantified—methyl through hexyl dithianes—at 1 picomole level per injection by single ion monitoring of the following ions 119,134,148,162,176,190 and 204. A library of 1 M compounds can be encoded by 20 tags, which translates into 20 pmoles of tags per 1 library compound, or a total of 20 μmoles of tags per library. If the average molecular weight of the tag does not exceed 300, for example, no more than 60 mg of dithiane-based tags can encode a 1 M compound library and still be analyzed with a generic GC MS.

As mentioned above, a critical advantage of this invention is that the "photo-development" of the library incubated with electron-transfer photosensitizer-receptor releases the lead compound (or a small "tag") into the solution. This can be useful for automation, because neither visualization of the positive binding results nor the mechanical separation of the winning beads is required.

Synthesis

Selected examples of aromatic ketones that can be used for amplification are given below:

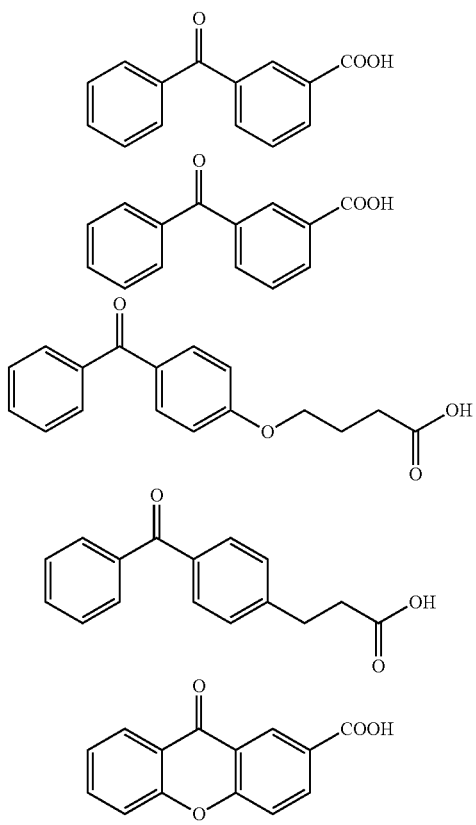

These ketones were masked by reaction with various nucleophiles. Exemplary adducts with substituted dithianes are shown below. These adducts are obtained by lithiating dithianes with butyl or tert-butyl lithium and reacting them with the ketones, as known in the art.

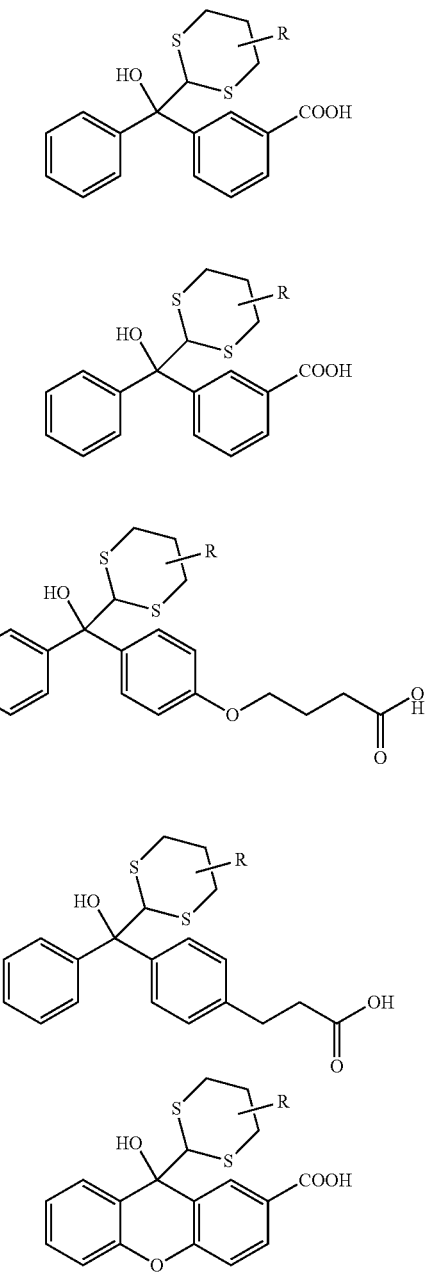

The R groups indicate various substituents, as known in the art and described herein. Exemplary R substituents include hydrogen, optionally-substituted straight chain, branched and cyclic C1-20 alkyl, alkenyl, or alkynyl groups where one or more of the C atoms can be substituted, or wherein one or more of the C, CH or $CH_2$ moieties can be replaced with O atoms, —CO— groups, —OCO— groups, N atoms, amine groups, S atoms or a ring structure, which ring structure can optionally contain one or more heteroatoms and which ring structure can be optionally substituted; and optionally substituted aromatic and nonaromatic ring structures, including rings that are fused to one or more other rings.

The carboxy-functionality was converted into N-hydroxysuccinimide ester for immobilization on the beads, dendrimers or surfaces displaying primary amino groups, for example.

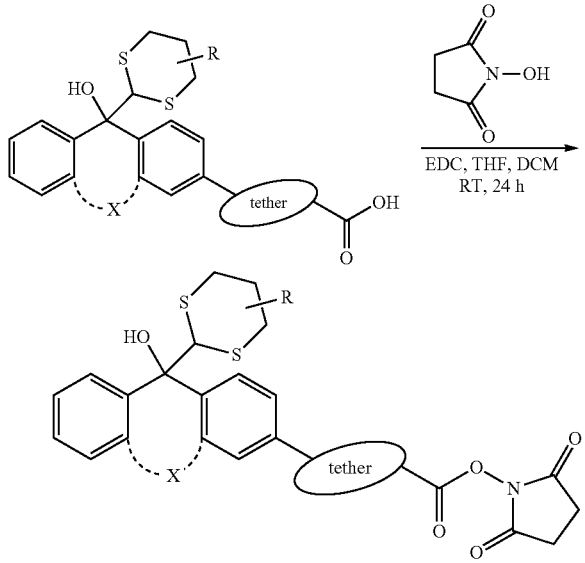

where "X" can be O, S, N, CR$_2$ or no group.

Alternatively, a ketone is immobilized on the bead/dendrimer and then reacted with dithiane. For example, Tenta-Gel, HL-Br, O-(2-Bromoethyl)polyethylene glycol polymer bound (Fluka) or Merrifield resin (Aldrich), is treated with phenolate of 3- or 4-hydroxybenzophenone and then reacted with 2-lithiated 5-substituted dithianes as previously described (Rutledge, A.; Abell, C.; Balasubramanian, S. The use of a dithiane-protected benzoin photolabile safety catch linker for solid-phase synthesis. Tetrahedron Lett. 1997, 38(7), 1227-1230; Lee H. B.; Balasubramanian, S. Studies on a Dithiane-Protected Benzoin Photolabile Safety Catch Linker for Solid-Phase Synthesis. J. Org. Chem. 1999, 64, 3454-3460). The lithiodithiane addition progress is followed by disappearance of the carbonyl stretch in IR and by NMR monitoring of the downfield doublet of the benzophenone's ortho protons. To avoid the false amplification signal due to unreacted residual benzophenones in the original beads, the complete conversion of benzophenone is ensured. If the lithiodithiane reaction is not 100% complete, small penetrating reducing agents, e.g NaBH$_4$, are used to reduce the residual benzophenones. Syntheses of rather bulky crown ether and calixarene-containing photolabile molecular hosts (Mitkin, O.; Wan, Y.; Kurchan, A.; Kutateladze, A. Synthesis of Dithiane-Based Photolabile Molecular Systems. Synthesis, 2001, (8), 1133-1142) indicates that carbonyl additions of lithiated dithianes are very efficient reactions and that lithiated dithiane drives the reaction to completion, especially when taken in slight excess. The actual dithiane loading is determined by elemental analysis of sulfur.

Addition of 5-substituted dithianes to tethered benzophenone produces one chiral (benzylic) center. With the given spatial separation of this center from the ligand displayed at the terminus, this does not constitute a stereochemical problem. As mentioned above, the cis-trans isomerism in 2,5-disubstituted dithiane is not an issue either, because in most cases of 5-substituted dithiane addition to carbonyls studied, the stereochemistry of addition is predominantly trans. Even if some reactions are less trans-stereoselective, cis-trans isomerism does not have any significant effect on the chemistry, given the large spatial separation of the dithiane from the ligand.

It has been shown that substituted dithianes containing hydroxy groups are lithiated using excess butyl lithium and added to ketones or aldehydes. In another embodiment, amino group-containing dithianes are synthesized and used with the lithiated addition reaction. This gives direct access to photolabile tethers with terminal amines as shown below.

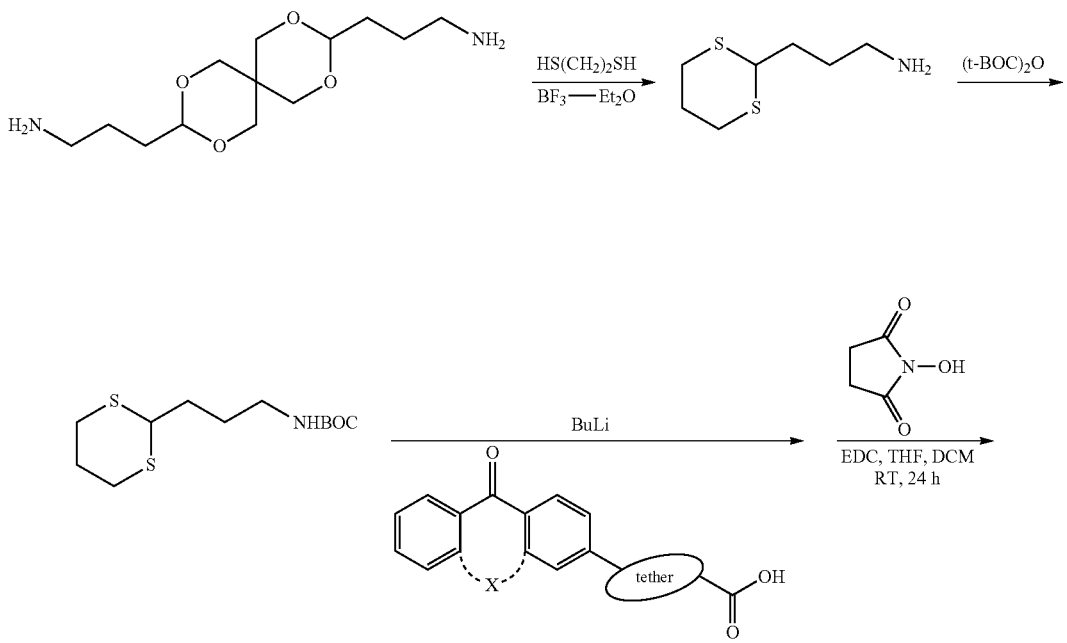

-continued

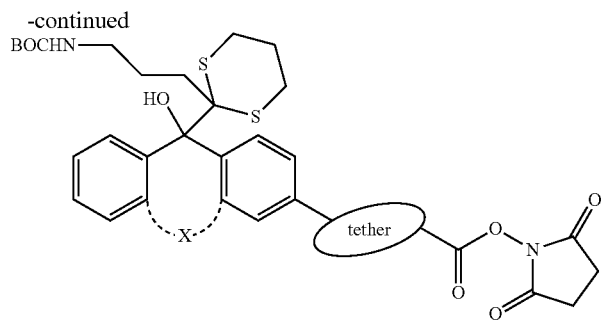

where "X" can be O, S, N, CR$_2$ or no group.

For characterization experiments, the benzophenone (BP) moiety is attached to TentaGel-Br as described above and then a series of incomplete dithiane additions is carried out, so that small percentage of tethered benzophenone groups is left untouched. The ratio of the immobilized dithiane adduct to immobilized free benzophenone is determined by NMR. The resulting beads are irradiated and the increase of free benzophenone groups at the expense of dithiane adducts are monitored by NMR or by calibrated UV. Samples with 10%, 1% and 0.1% residual benzophenone (the rest being the dithiane-benzophenone adduct) are prepared and irradiated, while monitoring the recovery of the tethered free benzophenone by NMR and UV. These experiments determine the threshold for intrinsic—i.e. no ligand attached—photoamplification in TentaGel-BP-dithiane system. After these characterization experiments, ligand-receptor interactions are studied using a well known complementary pair. In order to equip the receptor with a benzophenone moiety, 4- or 3-hydroxybenzophenone alkylated with a PEG chain carrying either maleimid or hydroxysuccinimide ester at the terminus is utilized. This methodology is well developed and now routine. For the initial testing of the concept the classical biotin-avidin technology was used, which is thoroughly documented in numerous sources, including a detailed volume in "Methods in Enzymology" (Methods in Enzymology. Wilchek, M.; Bayer, E. A. Editors; Academic Press, 1990, vol. 184). Biotin is commercially available in a form of hydroxysuccinimide ester with a PEG-chain incorporated into the tether. Two kinds of photolabile beads are prepared, one bearing biotin and the other—a placebo, for example, a PEG tethered single amino acid, lysine or an easily identifiable water soluble dipeptide. Avidin, a water soluble tetrameric glycoprotein, 67-68 kD, is available from commercial sources, for example, ImmunoPure® Avidin from Pierce Biotechnology. Avidin is outfitted with PEG-tethered benzophenone by incubation with its PEG-hydroxysuccinimidyl ester (BP-PEG-HSI) at pH 8 in PBS buffer. This conjugation technique is now routine. (Methods in Enzymology. Wilchek, M.; Bayer, E. A. Editors; Academic Press, 1990, vol. 184). Resulting BP-PEG-Avidin is purified by removing excess BP-PEG-HSI via dialysis or by chromatography on a Sephadex column as described in [Methods in Enzymology. Wilchek, M.; Bayer, E. A. Editors; Academic Press, 1990, vol. 184]. Benzophenone loading is determined by NMR. For this, the tetrameric benzophenone-conjugated avidin is treated with 5M guanidinium hydrochloride at pH=1.5 and the denatured monomer (128 amino acids) is analyzed by 1D proton NMR. If necessary, the disulfide bridge is reduced with β-mercaptoethanol or DTT. ImmunoPure® avidin contains several aromatic amino acids—Thr, Trp and Phe. The signals from aromatic protons of these residues are integrated and compared with the intensity of the downfield doublets of the ortho protons belonging to benzophenone. These resonances are easily discernible because the benzophenone's ortho protons appear downfield of 7.8 ppm, whereas the aromatic protons of Thr, Trp and Phe resonate upfield of 7.3 ppm.

A typical loading of the resin is on the order of 0.3±0.1 mmol g$^{-1}$. Approximately 100 mg of the biotinylated resin carrying at least 20 µmol of biotin, which is sufficient for confident NMR quantification in solution, and 100 mg of the negative control resin carrying placebo are mixed and equilibrated with small amounts of BP-PEG-avidin. The suspension is irradiated using medium pressure mercury lamp and Pyrex filter (cutoff λ>300 nm), the resulting solution is centrifuged or filtered, and the supernatant is analyzed using NMR after adding D$_2$O. To quantify the released biotin an external NMR tracer are added, for example calibrated amounts of sodium trimethylsilylethanesulfonate.

The sensitivity threshold, i.e. the extent of amplification at which biotin is fully released and yet the amount of the erroneously released placebo being below or near NMR detection limit is determined. For this, a series of experiments is performed starting with approximately 100 nmol of PB-PEG-avidin and then systematically lowering the amount of avidin.

The length of the PEG linker connecting the benzophenone to the beads must be sufficient for the subsequent sensitization of the neighboring tethers to occur efficiently. Therefore, variable length PEG tethers are tested with Merrifield resin to assess their effect on the efficiency of the photochemical chain release. The TentaGel-type PEG grafted resins are flexible enough to ensure near-solution state kinetics, so the tether length effects are less important. The length of the tether from the photocleavable unit to the displayed ligand should correlate with the length of the tether attaching benzophenone to the receptor in order for the photoinduced ET-sensitization to be efficient. Also, the tether to the ligand should be sufficiently long to diminish effects of the matrix on binding. Therefore, the length of the tether from the photolabile unit to the ligand is optimized. In order to assess the efficiency of the electron-transfer sensitization and identify the best combination of $\lambda_{max}$ and extinction coefficient, other substituted benzophenones are tested. Ideally, the excitation wavelength should be longer than the free photosensitizer in order to avoid damage to the ligands and other side reactions. However, shifting the wavelength deeper into the visible region has its own problems, the major being visible light sensitivity, which triggers premature reactions. Various substituted benzophenones with their $\lambda_{max}$ in the vicinity of 350 nm allow for optimum illumination wavelength. Utilization of 2-methyl-1,3-dithiane on average doubles the quantum yield of photoinduced cleavage. Methyldithiane adducts with various derivatives of 3- and 4-alkoxybenzophenone are synthesized using methods known in the art and the kinetics/quantum yields of their fragmentation is studied in a search for the most efficient system for the solid support chemistry. The lead compound is released with the attached dithiane-PEG unit. If desired, this appendage can be removed before the compound is analyzed. One way of doing this is to make the connection between the ligand and the dithiane-PEG stem solvolytically labile—after the photochemical detachment into N-silyl imine, reaction with lithiated methyldithiane furnishing primary amine, which is acylated through a DCC mediated coupling with an N-protected GABA (X=CH$_2$) or longer chain ω-aminoacid. Thus modified beads are used for combinatorial synthesis. All these steps have been optimized for solution chemistry of shorter tailed alkoxy benzophenones. Methyldithiane is used to improve the quantum yield of photo-fragmentation.

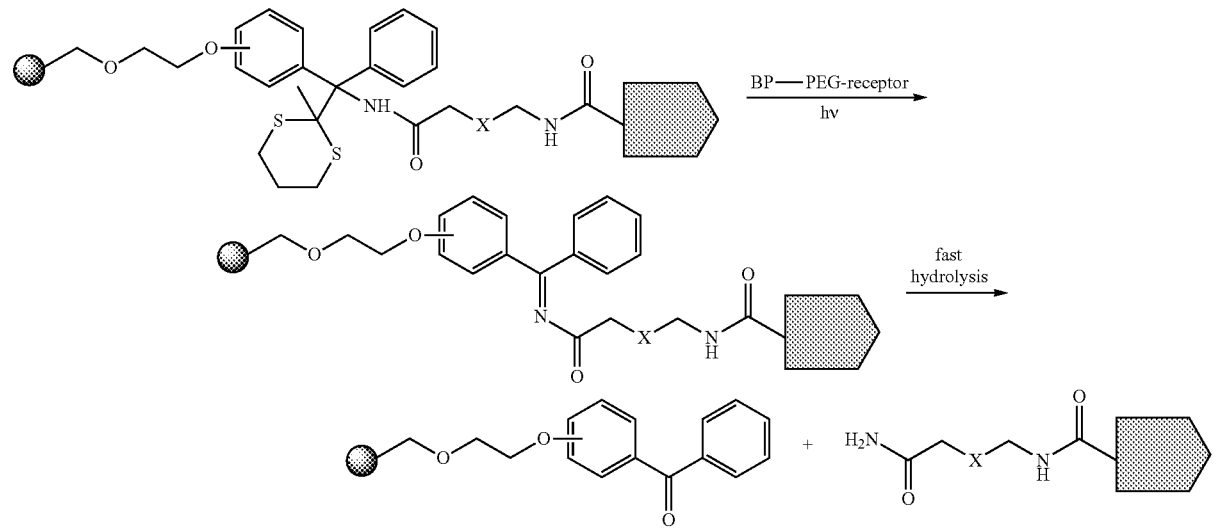

from the bead it can be handled via classical solution chemistry manipulations, as known in the art.

The dithiane-containing "appendage" can be altogether avoided—ligands can be tethered directly to the amino-group of the amino counterparts of Corey-Seebach adducts, bypassing dithiane. One exemplary synthesis is shown below:

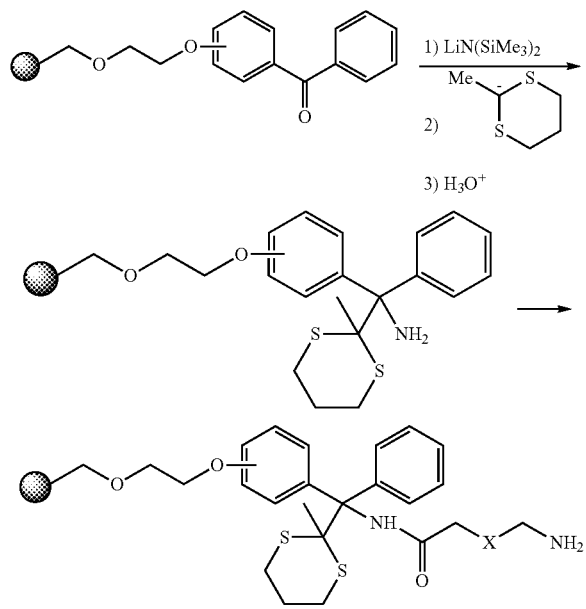

The general synthetic scheme involves immobilization of benzophenone on TentaGel-Br, conversion of the carbonyl "X" is any desired group or atom. The shaded rectangular shape indicates the ligand.

Binding of benzophenone-bearing receptor (BP-PEG-receptor) and irradiation triggers the departure of methyldithiane moiety, producing hydrolytically labile acyl imine. Fast hydrolysis releases the ligand tethered to GABA-NH$_2$ liberating the bead-tethered benzophenone, which carries the photochemical chain in the fashion described above.

The dithiane coupling allows for very fast release of the tethered ligand and produces benzophenone in the single (fast) photochemical step, whereas the amine tethering requires one additional solvolytic step to release the ligand after photofragmentation and to re-generate the sensitizer. At the same time the amine approach liberates the ligand free of the dithiane moiety (the by-product of the photo-fragmentation, methyldithiane, is a small hydrophobic compound, which can be easily removed by organic extraction or other means of separation). The photocleavable acylated amines are also more stable under strongly acidic conditions.

Alkoxybenzophenones are useful as sensitizers in part by the fact that alkoxy-substituted aryl ketones have π→π* triplet states, which are much less reactive toward hydrogen abstraction than benzophenones which have n→π* triplet excited states (Wagner, P. J.; Kemppainen, A. E.; Schott, H. N. Effects of ring substituents on the type II photoreactions of phenyl ketones. How interactions between nearby excited triplets affect chemical reactivity. *J. Am. Chem. Soc.*, 1973, 95(17), 5604-5614). This decreases undesirable cross-linking with the matrix. At the same time alkoxybenzophenones are still excellent electron-transfer sensitizers for dithianes. In preliminary studies 4,4'-dimethoxybenzophenone and its dithiane adduct were used to demonstrate that the π→π* state is capable of single electron transfer oxidation of the dithiane moiety, which triggers the fragmentation. If a small number of benzophenones nevertheless cross link with the displayed ligands, the modified ligands would be covalently attached to the bead, preventing them from exiting into the solution. Thus, an accidental cross-linking may slightly decrease the amplification coefficient, but it will not produce modified ligands in the solution to complicate the analysis and characterization of the lead ligands.

Vesicle or Liposome Example

Figure 2:
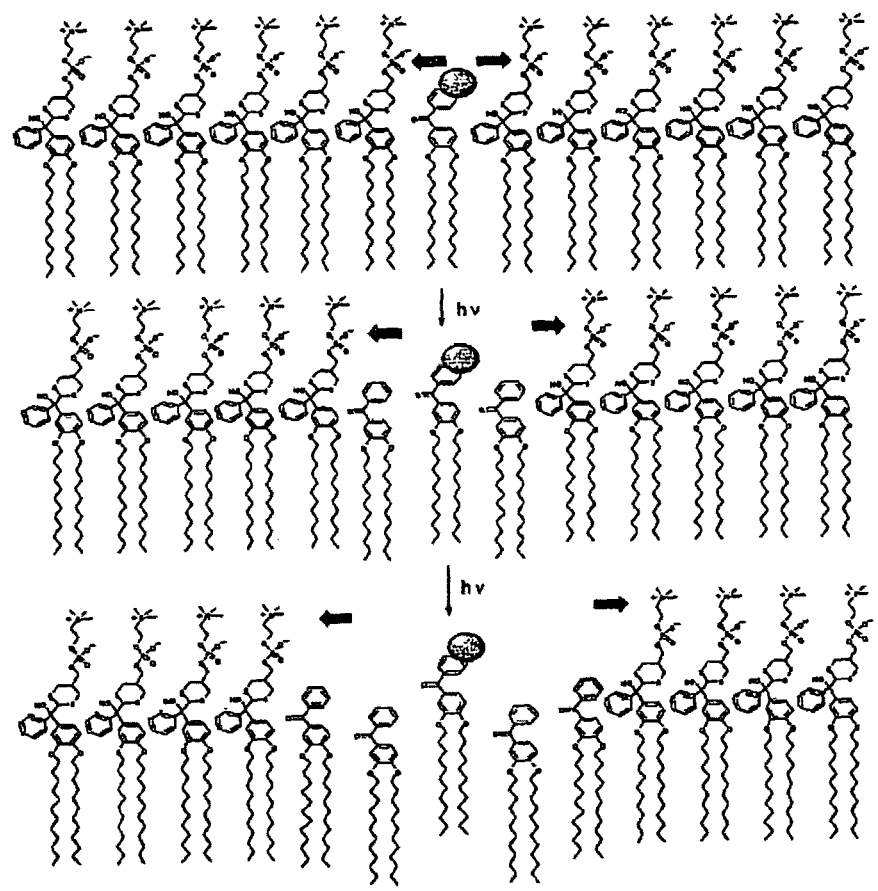
FIG. 2 shows an example of the invention using liposomes. The self-assembled mono- or bi-layer consists of photolabile amphiphiles containing a masked sensitizer. An external sensitizer (initiator) unmasks a proximal sensitizer, and the reaction continues, releasing the hydrophilic head group in the solution and "burning a hole" in the bilayer.

In this example, the objects used are unilamellar or multilamellar vesicles, or liposomes. When an amphiphile, based on a dithiane-benzophenone adduct is mixed with a small amount of amphiphile bearing "free" benzophenone photosensitizer as an "initiator" (shown in the top panel of FIG. 2), irradiation of the bilayer produces an ever increasing amount of (lipophilic) photosensitizer in the immediate proximity of the "initiator" (shown in the middle panel of FIG. 2). Disruption of lipid bilayer propagates in a concentric fashion, producing localized areas of instability (shown in the bottom panel of FIG. 2).

As in the previous example, this method is especially advantageous for the cases when the initial sensitization is triggered by an external event, such as insertion of an external photosensitizer into the lipid membrane as a result of targeting/molecular recognition or a similar event. It can be used to trigger the fusion of such liposomes with objects that can initiate the photochemical "chain", disrupting the membrane.

In this example, the masked photosensitizer (carrying a hydrophilic head group) is converted into the hydrophobic unmasked photosensitizer that is capable of carrying the chain, but also destabilizes the lipid bilayer. The amplification in this case is modulating the properties of the bilayer, which can be used for releasing materials (drugs) entrapped in the liposomes or for fusion with other membranes, for example.

Surface Modification

Figure 3:
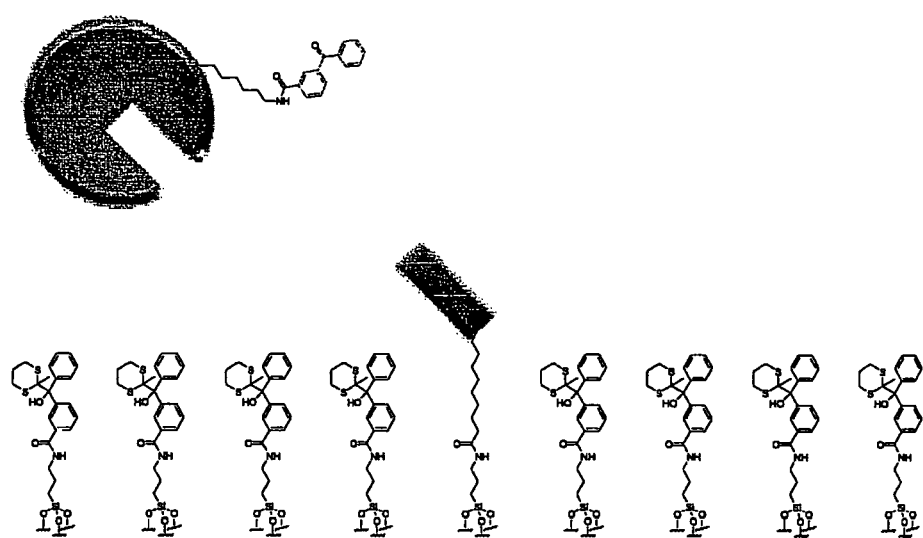
FIG. 3 shows a receptor coming toward a ligand bound to a surface.
Figure 4:
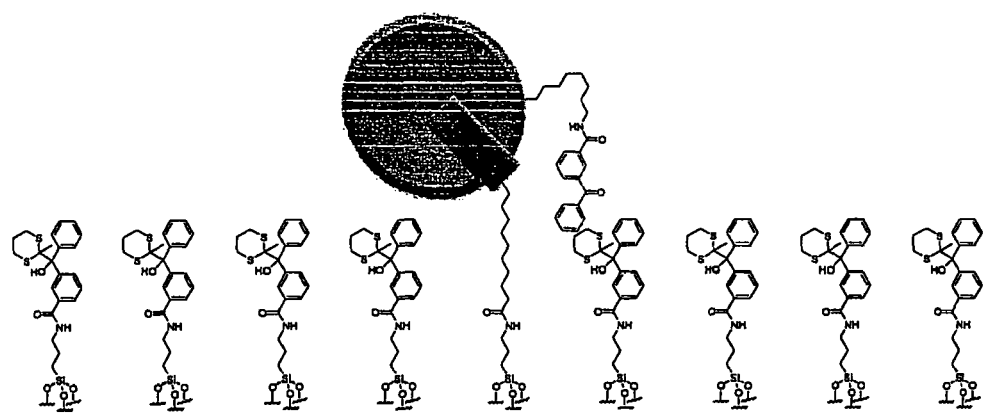
FIG. 4 shows binding of the ligand-receptor shown in FIG. 3.
Figure 5:
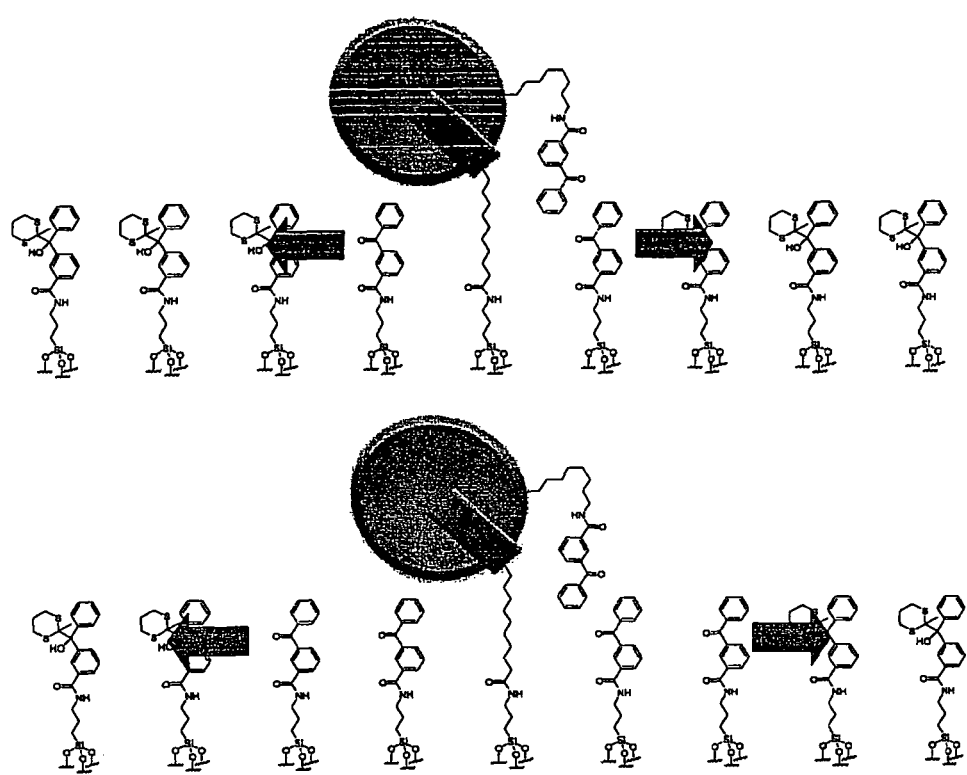
FIG. 5 continues the reaction shown in FIGS. 3 and 4 and shows photoinduced cleavage on the surface, which gives amplification of the released tag, dithiane, in the solution, and also modifies the photophysical and electrochemical properties of the surface.

In this example, the benzophenone-dithiane adduct (masked photosensitizer) is immobilized on the surface of ITO/quartz or other conductive material using existing chemistry. In the example shown in FIG. 3, aminopropyl tethers are used to bond the masked photosensitizer to the surface. The bulk of the surface is covered by the masked photosensitizer, with ligands of interest (shown as a rectangle) incorporated at a low density. The receptor (shown as a circle with a rectangular "binding site") under study is modified with a tethered benzophenone in situ using existing well developed methodology (as in photoaffinity labeling). FIG. 4 shows the receptor attracted to the surface by the exposed ligand, bringing the electron-transfer sensitizer (benzophenone) into the immediate proximity of the surrounding immobilized adducts. FIG. 5 shows the surface after irradiation. The tethered benzophenone photosensitizer induces fragmentation in the nearby adducts releasing more benzophenones in the immediate vicinity of the bound complex. As long as irradiation is continued, the concentric wave of benzophenone front propagates outward ("hole-burning"). The reductive organosulfur species is thus removed from the surface leaving behind a field of immobilized benzophenones. Electrochemical studies show that benzophenone-dithiane adducts oxidize at about +1 V (±0.2 vs. SCE). The benzophenone-exposed surface after the described amplifying photolysis has much higher oxidation potential, allowing for electroanalytical detection of the changes, using techniques known in the art. Methyldithiane is shown for simplicity here. A number of modified 5-substituted dithianes and dithiazines have been synthesized that are water soluble and can be used in the invention, for example, the structures shown below:

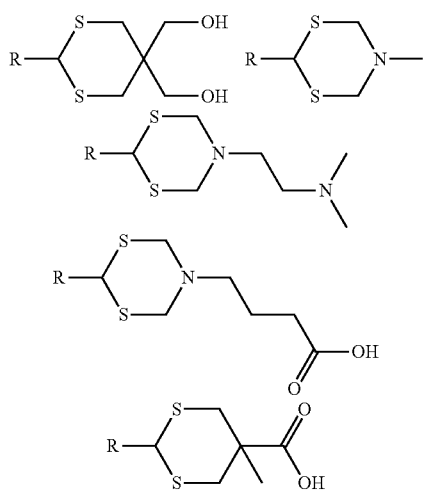

where R indicates any of the various useful groups known in the art and described herein. Exemplary R substituents include hydrogen, optionally-substituted straight chain, branched and cyclic C1-20 alkyl, alkenyl, or alkynyl groups where one or more of the C atoms can be substituted, or wherein one or more of the C, CH or $CH_2$ moieties can be replaced with O atoms, —CO— groups, —OCO— groups, N atoms, amine groups, S atoms or a ring structure, which ring structure can optionally contain one or more heteroatoms and which ring structure can be optionally substituted; and optionally substituted aromatic and nonaromatic ring structures, including rings that are fused to one or more other rings.

This approach is also useful for testing for multiple receptors/ligands, i.e. a series of ligands can be patterned onto a conductive surface such as an ITO surface, effectively furnishing an array of addressable electrochemical cells that are first incubated with the analyte, irradiated and the individual voltamograms are compared to identify the maximum change, which corresponds to the surface with the most cleavage of the masked photosensitizer.

This method can also be used for non-PCR based detection of DNA. It can be implemented in both "active" and "passive" modes. The active mode is described above, i.e. (a) the analyte DNA is tagged in solution with tethered benzophenone (a well developed chemistry); (b) the bulk dithiane-benzophenone modified ITO surface is patterned with oligonucleotides, complementary to the DNA of targeted analytes. In this case photoamplification leads to the dramatic change in oxidation potential of the addressable cells corresponding to the sought after analyte. In the passive mode, the surface is patterned with oligonucleotides as described above. These oligonucleotides are incubated with shorter complimentary oligonucleotides conjugated with benzophenone. The analyte, which in this case is not chemically modified, displaces the short complimentary oligonucleotides, removing benzophenone from the immediate vicinity of the dithiane adducts and thus preventing the photoamplification in the areas where binding actually occurred. All the other areas are photoamplified and therefore stripped of dithiane. The positive response of the passive mode system is the lack of amplification (as contrasted to the control cells undergoing dramatic change in oxidation potential).

Analysis of "positive hits" can also be done utilizing (i) fluorescent probes (e.g. partial replacement of benzophenone by highly fluorescent 2-amidothioxanthone—with the same net photochemistry) or (ii) by chemical analysis of dithiane-based tags in solution. The methodology can be modified and adopted to a variety of applications, as will be apparent to one of ordinary skill in the art using the disclosure herein.

Any system that cleaves when a cation-radical is formed can be used in the current invention. For example, Whitten's amino alcohols, or hydroxy ethers can be used. A general scheme, which includes dithianes as the masking group is shown below:

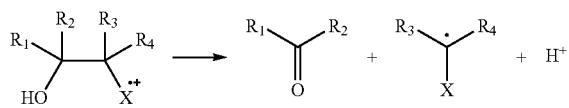

where the R's are the same or different and are any useful substituent, such as those described herein and those described for R above; and the X is a group capable of forming a cation-radical, for example, a heteroatom (O, N, S, etc.) or a π system such as alkenyl or aromatic. [Gaillard, E. R.; Whitten, D. G. *Acc. Chem. Res.* 1996; 29 292].

A further example of a useful cation radical reaction is photoinduced hydrolysis of acetals or thioacetals. In case R1-CO—R2 is an aromatic ketone capable of electron-transfer sensitization of its own release, another example of amplification.

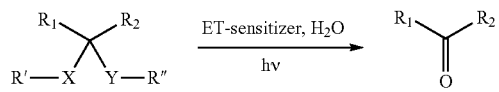

X,Y=oxygen or nitrogen or sulfur
R1, R2, R' and R" are the same or different and are any useful substituent as disclosed herein including useful substituents described as R above Photoamplified Fluorescence Turn-Off Assay In this embodiment of the invention, a masked photosensitizer, such as those described elsewhere herein, is mixed with a fluorescent molecule. This mixture is brightly fluorescent because the masked photosensitizer is not capable of quenching the fluorophore. When the photosensitizer is released and amplified, the photosensitizer quenches the emission of fluorophores very efficiently.

More specifically, upon irradiation of a system comprising a masked photosensitizer and a fluorescent molecule, the masking group is released from the masked photosensitizer. The unmasked photosensitizer is chosen so that it is capable of reducing the fluorescence of a fluorescent molecule. Using this embodiment, the reduction in fluorescence is a sensitive measure of the amount of amplification.

The fluorophor can be selected using one or more of the following criteria. (a) it does not significantly absorb light in the band used for the band reserved for the amplification photochemistry (e.g. the n→pi* absorption band of benzophenone is the vicinity of 340-370 nm); (b) it has a short fluorescence lifetime, (in one example less then 1 ns), which makes it very difficult to quench by species other than amplified sensitizer; for example it is quenched neither by dithianes nor by their benzophenone adducts; (c) it is a stable fluorophore, which is not easily photobleached; for this reason laser dyes are particularly suitable; (d) it is hydrophobic and is lacking any molecular recognition elements implicated in biological processes, which is to say that it is not expected to interfere with binding assays, and will not diffuse into the aqueous space reserved for molecular recognition chemistry.

Figure 6:
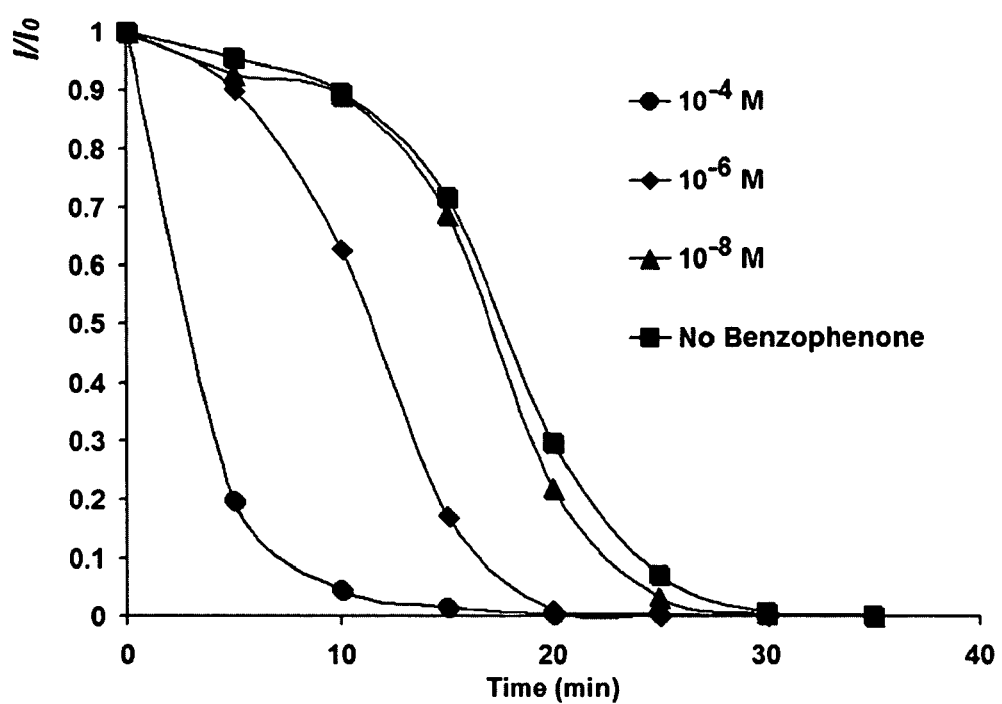
FIG. 6 shows amplified quenching of p-terphenyl emission as a result of benzophenone photoamplification. Initial concentrations of benzophenone are $10^{-4}$ M (◉), $10^{-6}$ M (◇), $10^{-8}$ M (△), no benzophenone added (▦). Masked benzophenone: $10^{-2}$ M; p-terphenyl: $2 \times 10^{-5}$ M.
Figure 7:
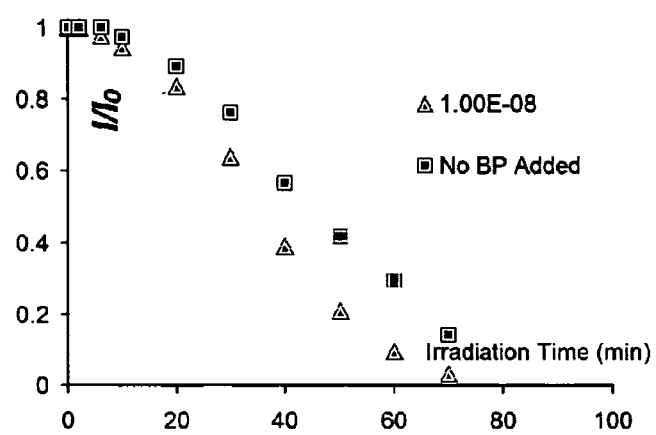
FIG. 7 shows amplified quenching of p-terphenyl emission as a result of benzophenone photoamplification in an organogel formed by gelating tert-butylbenzene with 4% octadecylurea. Initial concentrations of benzophenone are $10^{-8}$ M (△), no benzophenone added (▦). Masked benzophenone: $10^{-2}$ M; p-terphenyl: $2 \times 10^{-5}$ M.

FIG. 6 shows amplification of benzophenone in the masked benzophenone-methyldithiane adduct ($10^{-2}$ M) triggered by systematically diluted benzophenone initiator. (The emission of p-terphenyl, present at $2\times10^{-5}$ M is normalized to 1.0). As benzophenone is amplified in the solution, the emission of p-terphenyl is quenched by more than two orders of magnitude, offering a photochemical basis for a robust and ultra-sensitive fluorescence turn-off assay.

In one study, p-terphenyl is used as the fluorophor. Quaterphenyl and similar fluorophores can be used as well, and other fluorophors, as can be selected by one of ordinary skill in the art using the disclosure herewith. The selection of suitable fluorophors and sensitizers is easily carried out by one having ordinary skill in the art using the guidance provided here. Suitable fluorophores are selected based on the criteria listed above, including: high fluorescence quantum yield, relatively short singlet lifetime, and strong absorption in a part of the spectrum which is not overlapping with the excitation wavelength reserved for photoamplification of the sensitizer. Numerous examples of such fluorophores are known to one of ordinary skills in the art (hundreds of fluorescing compounds are tabulated in "Handbook of Photochemistry" by Murov, Carmichael and Hug).

Figure 12:
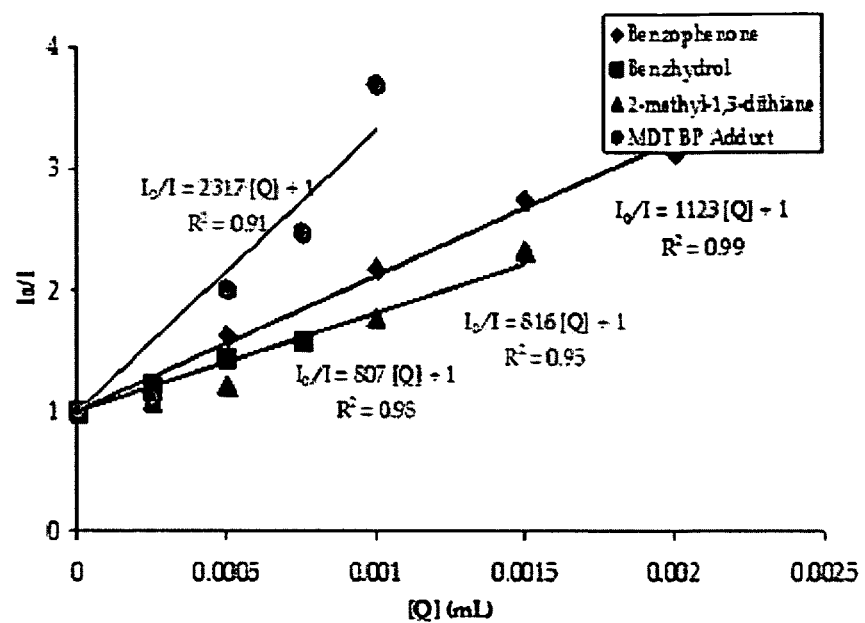
FIG. 12 shows the Stern-Volmer plot for fluorescence quenching of fluorene ($10^{-5}$ M), in $CH_2Cl_2$, by benzophenone benzhydrol, 2-methyl-1,3-dithiane, and 2-methyl-1,3-dithiane benzophenone adduct (MDT BP Adduct) to determine $K_{sv}$ for each quencher.
Figure 13:
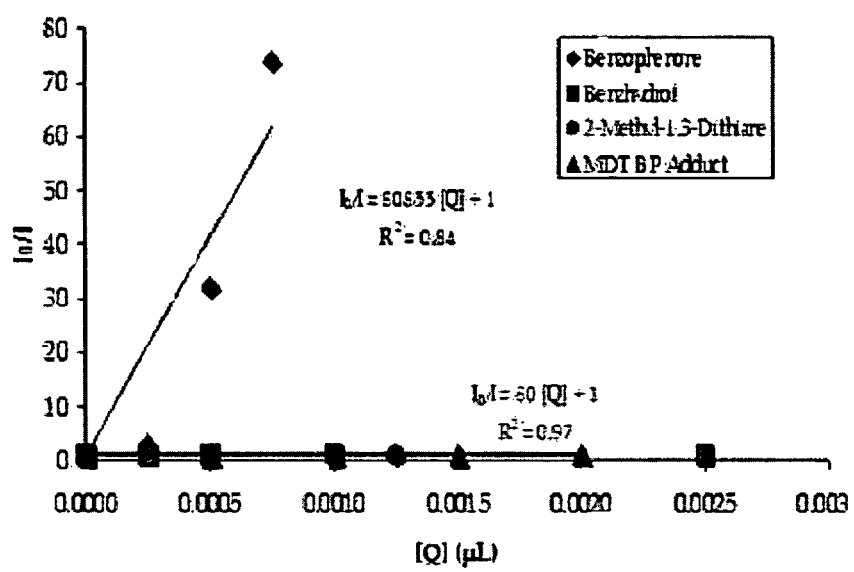
FIG. 13 shows the Stern-Volmer plot for fluorescence quenching of p-terphenyl ($10^{-5}$ M), in $CH_2Cl_2$, by benzophenone benzhydrol, 2-methyl-1,3-dithiane, and 2-methyl-1,3-dithiane benzophenone adduct (MDT BP Adduct) to determine $K_{sv}$ for each quencher. $K_{sv}$ for dithiane and benzhydrol was smaller than for MDT BP adduct.
Figure 14:
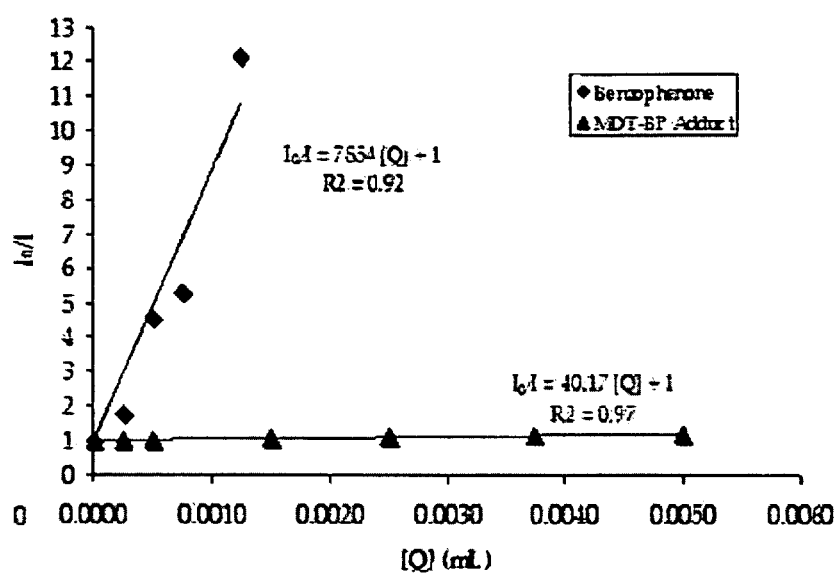
FIG. 14 shows the Stern-Volmer plot for fluorescence quenching of p-terphenyl ($10^{-5}$ M), in t-BuPh, by benzophenone and 2-methyl-1,3-dithiane benzophenone adduct (MDT BP Adduct) to determine $K_{sv}$ for each.

Fluorene was initially used as one example of fluorophor due to its high $\phi_{FL}$ of 0.68 and fluorescence lifetime ($\tau_{fl}$ of 10 ns in non-polar solvents. Initial studies (FIG. 12) showed benzophenone to be a very good quencher for fluorene (Ksv=1100 $M^{-1}s^{-1}$ in $CH_2Cl_2$), however the adduct proved to be an even more efficient quencher of fluorene ($K_{SV}$=2300 $M^{-1}s^{-1}$), rendering it not ideal. A fluorophore with a shorter lifetime (less prone to quenching by the masked sensitizer) was desired. Focus shifted to p-oligophenylenes particularly in p-terphenyl ($\Phi_{FL}$=0.84, $t_f$=0.95 ns), which strongly absorbs at λmax~280 nm ($\epsilon$~$3.5\times10^4$) with no absorption beyond 330 nm and p-quaterphenyl ($\Phi_{FL}$=0.81, $t_f$=0.92 ns).

p-Oligophenylenes are known as durable fluorophores, and commonly used as a dye in dye lasers due to their resistance to photobleaching, a desirable characteristic for this application. Quenching results for p-terphenyl (FIG. 13 in $CH_2Cl_2$, and FIG. 14 in t-butylbenzene (t-BuPh)) show it is very efficiently quenched by benzophenone ($K_{sv}$=80900 $M^{-1}$ $s^{-1}$ in $CH_2Cl_2$, 7800 $M^{-1}$ $s^{-1}$ in t-BuPh) whereas the effect of the adduct, 2-methyl-1,3-dithiane benzophenone adduct (MDT BP adduct) is significantly smaller ($K_{sv}$=80 $M^{-1}$ $s^{-1}$, 40 $M^{-1}$ $s^{-1}$ in t-BuPh). Quenching by free alkyl dithianes was found to be insignificant. Because p-quarterphenyl was not as efficiently quenched by benzophenone (1100 $M^{-1}$ $s^{-1}$ in t-BuPh) p-terphenyl was used an example as the fluorophore of choice.

Figure 8:
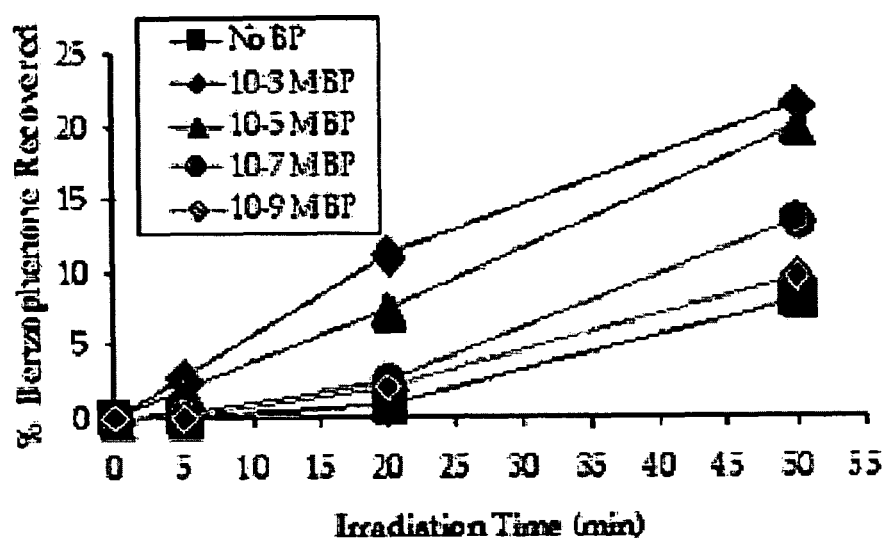
FIG. 8 shows recovery of benzophenone due to photoamplification of free sensitizer (BP), in $CH_3CN$, with starting concentrations of $10^{-3}$ M, $10^{-5}$ M, $10^{-7}$ M, $10^{-9}$ M, and no BP added.
Figure 9:
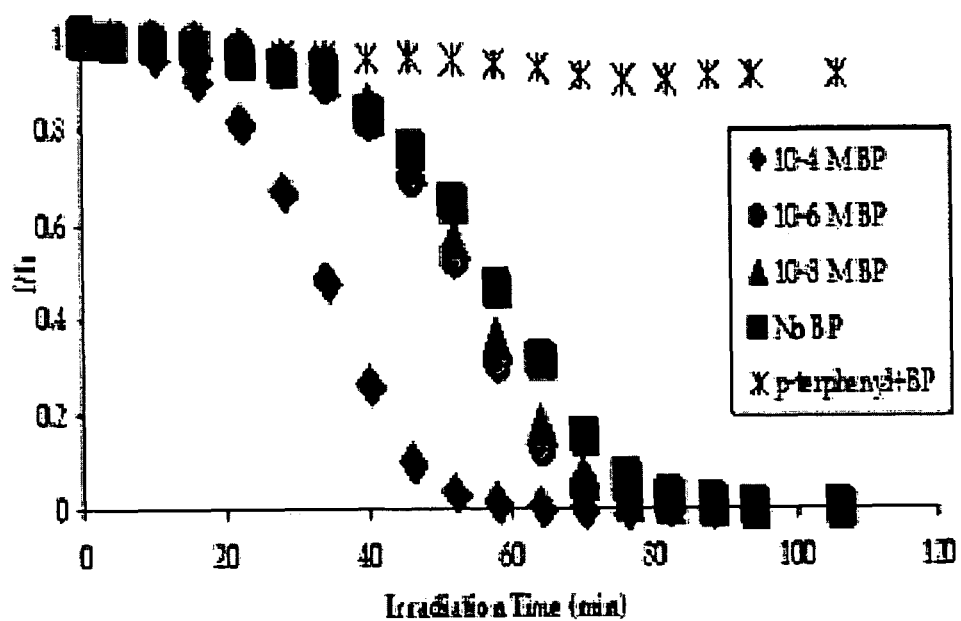
FIG. 9 shows normalized fluorescence quenching of p-terphenyl ($2 \times 10^{-5}$ M), in t-BuPh with $10^{-2}$ M MDT BP Adduct, due to photoamplification of quencher—benzophenone (BP)—with no BP, $10^{-8}$ M BP, $10^{-6}$ M BP, and $10^{-4}$ M BP. A control of p-terphenyl ($2 \times 10^{-5}$ M) and BP ($10^{-4}$ M) showed no quenching without photoamplification.
Figure 10:
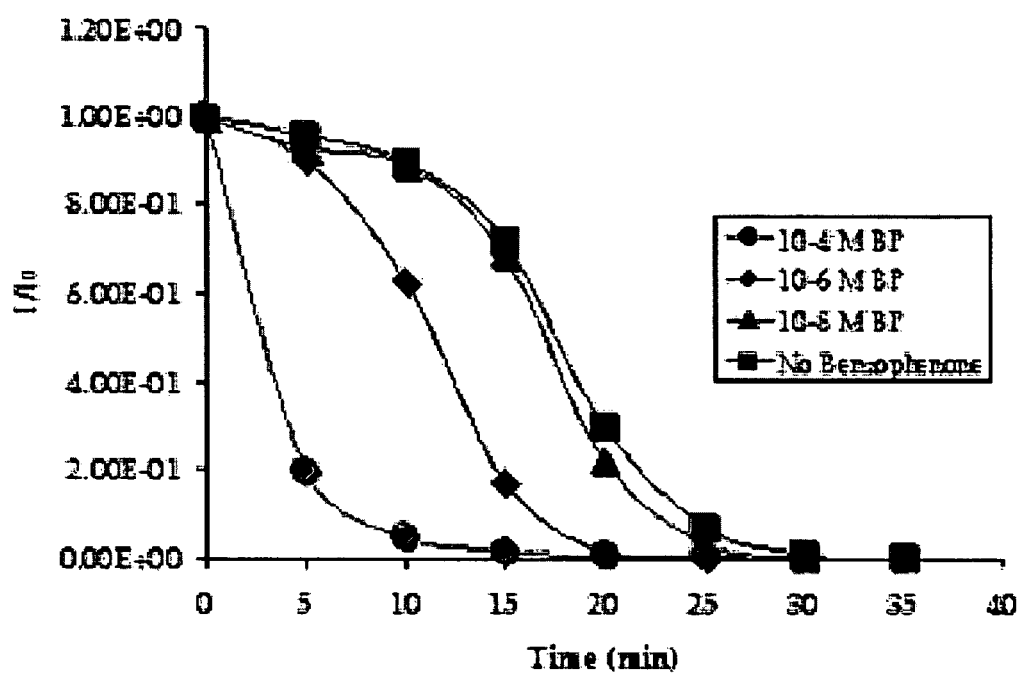
FIG. 10 shows normalized fluorescence quenching of p-terphenyl ($2 \times 10^{-5}$ M) in $CH_2Cl_2$ with $10^{-1}$ M 1,3-dithiane benzophenone adduct, due to photoamplification of quencher—benzophenone (BP)—with no BP, $10^{-8}$ M BP, $10^{-6}$ M BP, and $10^{-4}$ M BP. A control of p-terphenyl ($2 \times 10^{-5}$ M) and BP ($10^{-4}$ M) showed no quenching without photoamplification.

It has previously been shown that photoamplified unmasking of benzophenone is possible. Photofragmentation of MDT BP adduct, in $CH_3CN$, was followed by monitoring benzophenone recovery with $^1$H NMR to determine the minimum concentration of sensitizer (benzophenone) that could initialize photocleavage, and for which the results could be distinguished from a sample with no added sensitizer (fragmentation in this case can begin due to very low traces of benzophenone or self cleavage of the adduct). The detection limit was found to be between $10^{-7}$ and $10^{-9}$ M (FIGS. 8, 9, 10).

The amplified fluorescence quenching of p-terphenyl by benzophenone during photocleavage was also studied. FIGS. 9 and 10 show that, as benzophenone is amplified in solution, the emission of p-terphenyl is quenched by more than two orders of magnitude, offering a photochemical basis for a robust fluorescence turn-off assay. Apparently triplet sensitization of p-terphenyl, ET=58 kcal/mol by benzophenone (which has a triplet lying 10 kcal/mol higher) is not an issue. Even if such triplet energy transfer were to occur at a diffusion controlled rate, p-terphenyl is present at only $10^{-5}$ M concentration. The masked sensitizer is more than three orders of magnitude more concentrated ($10^{-2}$ M) and, as we have previously shown, quenches benzophenone triplet via electron transfer reduction at a near diffusion controlled rate ($10^9$ M$^{-1}$ s$^{-1}$). Thus, the fragmentation initiated by photoinduced electron transfer is by far the most efficient reaction channel, leading to successful amplified quenching of the fluorophore.

Compartmentalization in Organogels

In order to efficiently use the amplification methodology in devices, a compartmentalization strategy was developed. This strategy allows for free 3-dimensional collisional quenching in the solution and at the same time possesses structural elements, beneficial for fabrication of pixilated spatially addressable arrays. The compartmentalization strategy uses the photoamplified fluorescence approaches described here, both to turn the fluorescence "on" (recovery of fluorescence) and to turn the fluorescence "off" (quenching of fluorescence). Gelated solvents were developed to provide the structured support needed. As examples, dialkylureas were used as gelators for high boiling point solvents, such as tert-butylbenzene, as described in the literature: 3-5% of dioctadecylurea or 5% of dibutylurea produced stable and transparent organogels, which did not interfere with the amplification photochemistry while providing a structured support for the volume of solvent in which diffusion-based photoamplification was taking place. Refs: (a) George, M.; Tan, G.; John, V. T.; Weiss, R. G. Urea and Thiourea Derivatives as Low Molecular-Mass Organogelators. *Chem. Eur. J.* 2005, 11, 3243-3254. (b) George, M.; Weiss, R. G. Molecular Organogels. Soft Matter Comprised of Low-Molecular-Mass Organic Gelators and Organic Liquids. *Acc. Chem. Res.* 2006, 39, 489-497. A number of gelators can be used, as long as they do not have overlapping UV/VIS absorption and as long as they are not fluorescent. These gelators can be easily selected by one of ordinary skill in the art without undue experimentation using the disclosure provided herein.

The Pulse Field Gradient ("PFG") experiments were run to demonstrate that organogels prepared with 3-5% of the gelator do not impede the diffusion of benzophenone. These results are shown in Table 1.

TABLE 1

Diffusion Coefficients of 4-trifluoromethyl-benzophenone for organogels made in t-butyl benzene as determined by Pulse Field Gradient $^{19}$F NMR.

| % N-n-Octadecylurea | Diffusion Coefficient (cm$^2$ s$^{-1}$) |
| --- | --- |
| 0 | $6.50 \times 10^{-6}$ |
| 2 | $5.32 \times 10^{-6}$ |
| 4 | $5.60 \times 10^{-6}$ |
| 6 | $5.34 \times 10^{-6}$ |

The PFG NMR experiments allow for measuring diffusion coefficients of molecules of interest in complex mixtures, including gels. The successful photoamplification relies on adequate diffusion coefficients. The diffusion coefficients obtained for 4-trifluoromethylbenzophenone in gelated tert-butylbenzene and other solvents were within 10-15% of that in free (not gelated) solvents, which means that the gelation has no detrimental effect on photochemistry. At the same time the gelated solvent possessed the desired structural strength, allowing for mechanical pixilation, which is important for spatially addressable bioanalytical devices.

Figure 11:
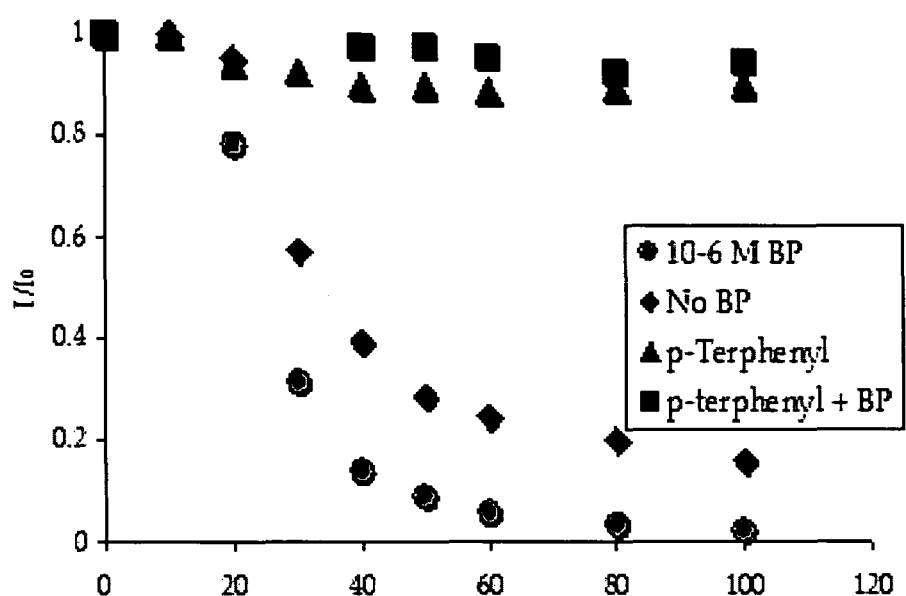
FIG. 11 shows normalized fluorescence quenching of p-terphenyl ($2 \times 10^{-5}$ M) due to photoamplification of quencher-benzophenone (BP)—in 4% N-n-octadecylurea organogels, made in t-BuPh containing $10^{-2}$ M MDT BP adduct, with no BP, $10^{-5}$ M MP, and $10^{-6}$ M BP. Controls of p-terphenyl ($2 \times 10^{-5}$ M) alone and with BP ($10^{-6}$ M) showed no interference between the gel and fluorescence as well as no significant fluorescence quenching without photoamplification.

As an example, 4% N-n-octadecylurea organogel prepared in t-butyl benzene containing $10^{-5}$ M p-terphenyl, $10^{-6}$ M benzophenone, and $10^{-2}$ M MDT BP adduct resulted in a stable organogel (data not shown). The photoamplified fluorescence quenching of p-terphenyl by benzophenone, during photocleavage was studied (FIG. 11). The organogels prepared above were irradiated for 100 minutes. The control was irradiated with only $10^{-5}$ M p-terphenyl and $10^{-6}$ M benzophenone. FIG. 11 also shows photoamplified fluorescence quenching with $10^{-5}$ M p-terphenyl, $10^{-6}$ M benzophenone, and $10^{-2}$ M MDT BP adduct.

Photoamplification in Ionic Liquids

The use of high boiling point liquids, such as tert-butylbenzene, allowed us to prevent fast evaporation from the chip. We further discovered that the amplification reaction is possible in ionic liquids, for example, in tetraalkylammonium, imidazolium or pyridinium salts carrying hydrophobic alkyl groups. Wadhawan Jay D; Wain Andrew J; Kirkham Andrew N; Walton David J; Wood Bill; France Robert R; Bull Steven D; Compton Richard G Electrocatalytic reactions mediated by N,N,N',N'-Tetraalkyl-1,4-phenylenediamine redox liquid microdroplet-modified electrodes: chemical and photochemical reactions In, and At the surface of, femtoliter droplets. J. Am. Chem. Soc. 2003, 125(37), 11418-29.

Ionic liquids are known to have extremely low vapor pressure. The higher homologs are not miscible with water. At the same time, photoinduced electron transfer was facilitated in ionic liquids as reported by Falvey (Falvey, D. E; Vieira R. C. Photo-induced electron transfer in room temperature ionic liquids: Charge stabilization and solvent mediation. Book of abstracts of the 234th ACS National Meeting, Boston, Aug. 19-23, 2007, ORGN 447). We have found that photoinduced amplification can be performed in ionic liquids. Gelation of ionic liquids has been described by Graetzel and co-workers. (Mohmeyer, N.; Kuang, D.; Wang, P.; Schmidt, H.-W.; Zakeeruddin, S. M.; Graetzel, M. An efficient organogelator for ionic liquids to prepare stable quasi-solid-state dye-sensitized solar cells. Journal of Materials Chemistry 2006, 16(29), 2978-2983). One example of a spatially addressable fluorescence turn-off assay embodiment is pixilated ionic liquids organogels.

Another use of ionic liquids for photoamplified bioanalytical methods is for electrochemical detection. Ionic liquids often possess wide electrochemical windows and are used extensively in electroanalytical chemistry (see for example, Nishi, Naoya; Imakura, Seiichi; Kakiuchi, Takashi. Wide Electrochemical Window at the Interface between Water and a Hydrophobic Room-Temperature Ionic Liquid of Tetrakis[3,5-bis(Trifluoromethyl)phenyl]borate. Analytical Chemistry (2006), 78(8), 2726-2731). Unmasking of the sensitizer dramatically changes the redox properties of the system which can be utilized in electrochemical detection of photoamplification. Again, as mentioned above, ionic liquids can be gelated and used in a form of pixilated bioanalytical array. Our experiments show that while the diffusion is slower in ionic liquids, it does not preclude the propagation of photoinduced fragmentation. The $^{19}$F PFG NMR measurements of diffusion of 4-(trifluoromethyl)benzophenone in N-methyl-N,N,N-trioctylammonium bis-triflylamide produced the translational diffusion coefficient of $9 \times 10^{-7}$ cm$^2$ s$^{-1}$, which is still adequate for bimolecular collisional quenching of triplet benzophenone, necessary for the photoamplification. N-Methyl-N,N,N-trioctylammonium bis-triflylamide is the most viscous ionic liquid which we tested in our experiments. Other, much less viscous ionic liquids, for example N,N-dimethyl-N,N-dihexylammonium bis-triflylamide, performed even better.

Although the description herein contains many specificities, these should not be construed as limiting the scope of the invention, but as merely providing illustrations of some of the preferred embodiments of the invention. For example, photosensitizers for masking, reaction photosensitizers, electron-transfer sensitizers, specific binding pairs, molecules of interest and masking groups other than those specifically exemplified herein may be used, as known to one of ordinary skill in the art without undue experimentation. In addition, chemical synthesis methods to attach all groups described herein, including masking groups to photosensitizers, members of specific binding pairs to various groups, and masked photosensitizers to surfaces are known to one of ordinary skill in the art. Useful linkages between groups are also within the skill of one of ordinary skill in the art. Additional embodiments are within the scope of the invention described in the specification and within the following exemplary claims.

When a group of substituents is disclosed herein, it is understood that all individual members of those groups and all subgroups, including any isomers and enantiomers of the group members, and classes of molecules that can be formed using the substituents are disclosed separately. When a molecule is claimed, it should be understood that molecules known in the art including the molecules disclosed in the references disclosed herein are not intended to be included. In particular, it should be understood that any molecule for which an enabling disclosure is provided in any reference cited in this specification is to be excluded from the claims herein if appropriate. When a Markush group or other grouping is used herein, all individual members of the group and all combinations and subcombinations possible of the group are intended to be individually included in the disclosure. Unless otherwise indicated, when a molecule is described and/or claimed herein, it is intended that any ionic forms of that molecule, particularly carboxylate anions and protonated forms of the molecule as well as any salts thereof are included in the disclosure. Counter anions for salts include among others halides, carboxylates, carboxylate derivatives, halogenated carboxylates, sulfates and phosphates. Counter cations include among others alkali metal cations, alkaline earth cations, and ammonium cations.

Every formulation or combination of components described or exemplified can be used to practice the invention, unless otherwise stated. Specific names of molecules are intended to be exemplary, as it is known that one of ordinary skill in the art can name the same molecules differently. When a molecule is described herein such that a particular isomer or enantiomer of the molecule is not specified, for example, in a formula or in a chemical name, that description is intended to include each isomer and enantiomer of the molecule described individually or in any combination. One of ordinary skill in the art will appreciate that methods, device elements, starting materials, synthetic methods, and detection methods other than those specifically exemplified can be employed in the practice of the invention without resort to undue experimentation. All art-known functional equivalents, of any such methods, starting materials, synthetic methods, and detection methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

In general the terms and phrases used herein have their art-recognized meaning, which can be found by reference to standard texts, journal references and contexts known to those skilled in the art. The specific definitions are provided to clarify their specific use in the context of the invention.

All patents and publications mentioned in the specification are indicative of the levels of skill of those skilled in the art to which the invention pertains.

One skilled in the art would readily appreciate that the present invention is well adapted to carry out the objects and obtain the ends and advantages mentioned, as well as those inherent therein. The molecules and methods and accessory methods described herein as presently representative of preferred embodiments are exemplary and are not intended as limitations on the scope of the invention. Changes therein and other uses will occur to those skilled in the art, which are encompassed within the spirit and scope of the invention.

All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention. U.S. provisional application 60/697,732, filed Jul. 8, 2006, from which this application claims priority, is incorporated by reference in its entirety.

REFERENCES

Schoevaars, A. M.; Kruizinga, W.; Zijlstra, R. W. J.; Veldman, N.; Spek, A. L.; Feringa, B. L. *J. Org. Chem.* 1997, 62, 4943.

Kurchan, A. N.; Kutateladze, A. G. *Org. Lett.,* 2002, 4, 4129.

McHale, W. A.; Kutateladze A. G. An Efficient Photo-SET-Induced Cleavage of Dithiane-Carbonyl Adducts and Its Relevance to the Development of Photoremovable Protecting Groups for Ketones and Aldehydes. *J. Org. Chem.,* 1998, 63, (26), 9924-9931. [DOI: 10.1021/jo981697y]

Vath, P.; Falvey, D. E.; Barnhurst, L. A.; Kutateladze, A. G. Photoinduced C—C Bond Cleavage in Dithiane-Carbonyl Adducts: A Laser Flash Photolysis Study. *J. Org. Chem.,* 2001, 66, (8), 2886-2890. [DOI: 10.1021/jo010102n]

Mitkin, O. D.; Kurchan, A. N.; Wan, Y.; Schiwal, B. F.; Kutateladze, A. G. Dithiane and Trithiane-Based Photolabile Scaffolds for Molecular Recognition. *Org. Lett.*, 2001, 3, (12), 1841-1844. [DOI: 10.1021/ol015933u]

Ci, X.; Whitten, D. G. Photochemical dehydrofragmentation reactions: importance of donor and acceptor structure in determination of reactivity in radical ion pairs formed in electron transfer photoreactions. *J. Am. Chem. Soc.* 1987, 109, 7215-7217.

Ci, X.; Whitten, D. G. Photofragmentation via single-electron transfer: selective labilization of carbon-carbon bonds in amino alcohols with several bonds between heteroatom substituents. *J. Am. Chem. Soc.* 1989, 111, 3459-3461.

Wan, Y.; Kurchan, A. N.; Barnhurst L. A.; Kutateladze, A. G. Direct Transformation of 1,3-Dihalides into Dithianes and Dithiepins via a Novel One Pot Reaction with Carbon Disulfide and Sodium Borohydride. *Org. Lett.*, 2000, 2, (8), 1133-1135. [DOI: 10.1021/ol005705k]

Gyenes, F.; Bergmann, K. E.; Welch, J. T. Convenient Access to Primary Amines by Employing the Barbier-Type Reaction of N-(Trimethylsilyl)imines Derived from Aromatic and Aliphatic Aldehydes. *J. Org. Chem.* 1998, 63, 2824.

Barnhurst, L. A.; Wan, Y.; Kutateladze A. G. Efficient Electrochemical Deprotection of Carboxylic and Amino Acids from Their 2-(Hydroxymethyl)-1,3-dithiane (Dim) Esters. *Org. Lett.*, 2000, 2, (6), 799-801. [DOI: 10.1021/ol005537w]

Wan Y., Barnhurst, L. A.; Kutateladze A. G. Photooxidation of Methyldithiepins into Dithiepin Carboxaldehydes in Carbon Tetrachloride. *Org. Lett.* 1999, 1 (6), 937-939. [DOI: 10.1021/ol990870p]

Wan, Y.; Kurchan, A. N.; Kutateladze, A. G. Photoinduced 1,3-Proton Shift in Methyldithiepines as a Potential Way of Modulating Hyperpolarizabilities. *J. Org. Chem.*, 2001, 66, (5), 1894-1899. [DOI: 10.1021/jo005707i]

Mitkin, O.; Wan, Y.; Kurchan, A.; Kutateladze, A. Synthesis of Dithiane-Based Photolabile Molecular Systems. *Synthesis*, 2001, (8), 1133-1142.

Wan, Y.; Mitkin, O.; Barnhurst L.; Kurchan, A.; Kutateladze, A. Molecular Assembly and Disassembly: Novel Photolabile Molecular Hosts. *Org. Lett.*, 2000, 2, (24), 3817-3819. [DOI: 10.1021/ol006692d]

Barnhurst, L. A.; Kutateladze, A. G. Synthesis and Liquid Membrane Transport Properties of Photolabile Molecular Clips Based on Dithiane-Spiro-Crown Ethers. *Org. Lett.*, 2001, 3, (17), 2633-2635. [DOI: 10.1021/ol016309k]

Wan, Y.; Angleson, J. K.; Kutateladze, A. G. Liposomes from Novel Photolabile Phospholipids: Light-Induced Unloading of Small Molecules as Monitored by PFG NMR. *J. Am. Chem. Soc.*, 2002, 124, (20), 5610-5611. [DOI: 10.1021/ja016874i]

Kurchan, A. N.; Kutateladze, A. G. Amino Acid-Based Dithiazines: Synthesis and Photofragmentation of Their Benzaldehyde Adducts. *Org. Lett.*, 2002, 4, (23), 4129-4131. [DOI: 10.1021/ol0268790]

Juaristi, E.; Gonzalez, E. A.; Pinto, B. M.; Johnson, B. D.; Nagelkerke, R. The existence of Second-Row Anomeric Interactions. Conformational Analysis of 2-Substituted 5-methyl-5-aza-1,3-dithiacyclohexanes. *J. Am. Chem. Soc.* 1989, 111, 6745-6749.

Larock, R. C.; Comprehensive organic transformations. VCH Publishers Inc., 1989, p. 409-410.

Portnyagina, V. A.; Fedoseeva, V. N.; Kolyadich, E. P. Synthesis and properties of 1,3-dimercapto derivatives of aromatic carboxylic acids and o-aminophenol. *Ukr. Khim. Zh.* 1981, 47(8), 857-61;

Portnyagina, V. A.; Fedoseeva, V. N.; Kolyadich, E. P. β-Dithiols as derivatives of aliphatic carboxylic acids. *Ukr. Khim. Zh.* 1981, 47(9), 962-4.

Borgulya, J.; Daly, J. J.; Schönholzer, P.; Bernauer, K. Rearrangement of Derivatives of 1,3-Dithiane-5-amine into Bicyclic 2-Thiazolidines. Crystal Structures of cis- and trans-1-(2-Aryl-1,3-dithian-5-yl)-2-thioureas and cis- and trans-5-Aryl-3-imino-7,7a-dihydro-1H,3H,5H-thiazolo[3,4-c]thiazoles. *Helv. Chim. Acta,* 1984, 67, 1827-1842.

Salvatore, R. N.; Nagle, A. S.; Jung K. W. Cesium Effect: High Chemoselectivity in Direct N-Alkylation of Amines. *J. Org. Chem.* 2002, 67, 674-683

Conn, M. M.; Rebek, J., Jr. Self-Assembling Capsules. *Chem. Rev.* 1997, 97(5), 1647-1668.

Rebek, J., Jr. Reversible Encapsulation and Its Consequences in Solution. *Acc. Chem. Res.* 1999, 32(4), 278-286.

Chang, S. K.; Hamilton, A. D. Molecular recognition of biologically interesting substrates: synthesis of an artificial receptor for barbiturates employing six hydrogen bonds. *J. Am. Chem. Soc.* 1988, 110, 1318-19.

Kita, K.; Kida, T.; Nakatsuji, Y.; Ikeda, I. Molecular Design of C-Pivot Tripodal Ligands: Importance of the Glycerol Structure for Effective Complexation toward Alkali Metal Cations. *J Org. Chem.* 1997, 62(23), 8076-8081.

Dale, J.; Fredriksen, S. B. Reactivity of neopentyl-like compounds in the synthesis of branched polyethers. Acta Chem. Scand., 1992, 46(3), 278-82.

Esnault, J.; Mallet, J.-M.; Zhang, Y.; Sinay, P.; Le Bouar, T.; Pincet, F.; Perez, E. New highly hydrophobic Lewis X glycolipids: synthesis and monolayer behavior. *Eur. J. Org. Chem.* 2001, 2, 253-260.

Seidel, S. R.; Stang, P. J. High-Symmetry Coordination Cages via Self-Assembly. *Acc. Chem. Res.* 2002, 35(11), 972-983.

Fukunaga, M.; Sugawara, T.; Oki, M. Alkylation of 1,3,5-trithianes. *Chem. Lett.* 1972, (1), 55-58.

Rutledge, A.; Abell, C.; Balasubramanian, S. The use of a dithiane-protected benzoin photolabile safety catch linker for solid-phase synthesis. Tetrahedron Lett. 1997, 38(7), 1227-1230.

Lee H. B.; Balasubramanian, S. Studies on a Dithiane-Protected Benzoin Photolabile Safety Catch Linker for Solid-Phase Synthesis. *J. Org. Chem.* 1999, 64, 3454-3460.

Methods in Enzymology. Wilchek, M.; Bayer, E. A. Editors; Academic Press, 1990, vol. 184

Wagner, P. J.; Kemppainen, A. E.; Schott, H. N. Effects of ring substituents on the type II photoreactions of phenyl ketones. How interactions between nearby excited triplets affect chemical reactivity. *J. Am. Chem. Soc.*, 1973, 95(17), 5604-5614

Sarkar, S. K.; Garigipati, R. S.; Adams, J. L.; Keifer, P. A. An NMR Method To Identify Nondestructively Chemical Compounds Bound to a Single Solid-Phase-Synthesis Bead for Combinatorial Chemistry Applications. *J. Am. Chem. Soc.* 1996, 118, 2305-2306.

Brenner, S.; Lerner, R. A. Encoded Combinatorial Chemistry. *Proc. Natl. Acad. Sci. USA,* 1992, 89, 5381-5383.

Ohlmeyer, M. H. J.; Swanson, R. N.; Dillard, L. W.; Reader, J. C.; Asouline, G.; Kobayashi, R.; Wigler, M.; Still, W. C. *Proc. Natl. Acad. Sci. USA,* 1993, 90, 10922-10926.

Nestler, H. P.; Bartlett, P. A. Still, W. C. A General Method for Molecular Tagging of Encoded Combinatorial Chemistry Libraries. *J. Org. Chem.* 1994, 59, 4723-4724

JACS, 2005, 127, 12458

JOC, 1998, 63, 9924

JOC, 2001, 66, 2890

JOC, 2003, 68, 8236

Org. Lett., 2007, 9, 1077
PNAS, 2006, 103, 139179
JACS, 2006, 128, 14794
Murov, Handbook of Photochemistry, Marcel Dekker, 1993
Angew. Chem., 2007, 46, 6137
Spectrochimica Acta, A, 2000, 56, 783-795.
New J. Phys., 2004, 6, 88
Applied Physics, 1977, 13, 267-269.
Chem. Eur. J. 2005, 11, 3243-3254
Acc. Chem. Res., 2006, 39, 489-497

We claim:

1. A method of amplified fluorescence quenching comprising:
    (a) providing a plurality of masked photosensitizers, each masked photosensitizer having a masking group bonded to a quenching photosensitizer through a releasable covalent bond which disrupts the conjugation of the quenching photosensitizer;
    (b) providing a fluorophor in quenching proximity to a first masked photosensitizer;
    (c) providing a reaction photosensitizer in releasing proximity to a masked photosensitizer, exciting the reaction photosensitizer with photoradiation, whereby the reaction photosensitizer releases the masking group from a masked photosensitizer, forming an unmasked photosensitizer;
    (d) exciting the unmasked photosensitizer with photoradiation, whereby this excited unmasked sensitizer induces fragmentation in a masked photosensitizer, inducing release of the masking group from the first masked photosensitizer, producing a quenching photosensitizer which (1) reduces the fluorescence of the fluorophor and (2) induces the release of the masking group from another masked photosensitizer; and
    (e) repeating step (d).

2. The method of claim 1, wherein inducing release of the masking group from the masked photosensitizer in step is performed by exciting the first masked photosensitizer with photoradiation at a cleaving wavelength.

3. The method of claim 1, wherein the photosensitizer is selected from the group consisting of: benzophenone, substituted benzophenone, xanthone, anthraquinone, and any sensitizer which has an excited state capable of oxidizing the masking group.

4. The method of claim 1, wherein the fluorophor is a laser dye.

5. The method of claim 4, wherein the fluorophor is p-terphenyl.

6. The method of claim 1, wherein the fluorophor is a polyphenyl, which includes biphenyl, and quaterphenyl, or any fluorophore not absorbing UV/Vis light in the vicinity of photoamplification wavelength.

7. The method of claim 1, wherein the masking group is a member of the group consisting of: dithiane, trithiane, dithiazine, tert-alkyl, nitrile, carboxamide, and other radical leaving groups.

8. The method of claim 1, wherein the plurality of masked photosensitizers is attached to a support.

9. The method of claim 8, wherein the support is a dendrimer, particle, surface or liposome.

10. The method of claim 9, wherein the surface is selected from the group consisting of: conductive, semi-conductive, or non-conductive.

11. The method of claim 1, wherein at least one of the plurality of photosensitizers is attached to a first member of a ligand-receptor pair and the reaction photosensitizer is attached to the second member of a ligand-receptor pair.

12. The method of claim 1, wherein the masked photosensitizers and fluorophors are present in a gelated solvent.

13. The method of claim 12, wherein the gelated solvent is organic.

14. The method of claim 13, wherein the gelated organic solvent is selected from the group consisting of: alkanes, such as hexane, heptane, octane, nonane, decane and their isomers, benzene, substituted benzenes including tert-butylbenzene, bis-alkylbenzenes, tri-alkylbenzenes, dichlorobenzene and other high boiling point lipophilic solvents.

15. The method of claim 12, wherein the gelated solvent is an ionic liquid.

16. The method of claim 15, wherein the ionic liquid contains one or more hydrophobic alkyl groups.

17. The method of claim 16, wherein the ionic liquid is a tetraalkylammonium or imidazolium salt.

* * * * *